US012636397B2

(12) United States Patent
Kumpf

(10) Patent No.: US 12,636,397 B2
(45) Date of Patent: May 26, 2026

(54) SCENT DIFFUSING SYSTEM

(71) Applicant: Sonos, Inc., Santa Barbara, CA (US)

(72) Inventor: Adam Kumpf, Delaware, OH (US)

(73) Assignee: Sonos, Inc., Goleta, CA (US)

( * ) Notice: Subject to any disclaimer, the term of this patent is extended or adjusted under 35 U.S.C. 154(b) by 416 days.

(21) Appl. No.: 18/096,423

(22) Filed: Jan. 12, 2023

(65) Prior Publication Data

US 2023/0218795 A1 Jul. 13, 2023

Related U.S. Application Data

(60) Provisional application No. 63/298,887, filed on Jan. 12, 2022.

(51) Int. Cl.
*A61L 9/03* (2006.01)
(52) U.S. Cl.
CPC ........... *A61L 9/035* (2013.01); *A61L 2209/11* (2013.01); *A61L 2209/133* (2013.01)
(58) Field of Classification Search
CPC ................. A61L 9/035; A61L 2209/11; A61L 2209/133; A61L 9/14; F24F 8/50
See application file for complete search history.

(56) References Cited

U.S. PATENT DOCUMENTS

| | | | |
|---|---|---|---|
| 5,440,644 A | 8/1995 | Farinelli et al. | |
| 5,761,320 A | 6/1998 | Farinelli et al. | |
| 5,923,902 A | 7/1999 | Inagaki | |

| | | | |
|---|---|---|---|
| 6,032,202 A | 2/2000 | Lea et al. | |
| 6,256,554 B1 | 7/2001 | DiLorenzo | |
| 6,404,811 B1 | 6/2002 | Cvetko et al. | |
| 6,469,633 B1 | 10/2002 | Wachter | |
| 6,522,886 B1 | 2/2003 | Youngs et al. | |
| 6,611,537 B1 | 8/2003 | Edens et al. | |
| 6,631,410 B1 | 10/2003 | Kowalski et al. | |
| 6,757,517 B2 | 6/2004 | Chang | |

(Continued)

FOREIGN PATENT DOCUMENTS

| | | |
|---|---|---|
| EP | 1389853 A1 | 2/2004 |
| WO | 200153994 | 7/2001 |
| WO | 2003093950 A2 | 11/2003 |

OTHER PUBLICATIONS

AudioTron Quick Start Guide, Version 1.0, Mar. 2001, 24 pages.

(Continued)

*Primary Examiner* — Qingzhang Zhou

(57) ABSTRACT

Example techniques described herein involve a scent diffusing system. The system can include scent diffusing device(s), playback device(s), and controller device(s). The controller device may display on a graphical interface a representation of a first scent diffusing device and receive one or more inputs selecting the representation of the first scent diffusing device and a particular scent for the first scent diffusing device to release. At least one setting for the particular scent may be displayed which may include a scent release time. A selection of the at least one setting may be received, and the controller device may send a message to the first scent diffusing device including information indicating the scent to release and the selected at least one setting. The controller device can cause the first scent diffusing device to release the particular scent at the release time.

20 Claims, 13 Drawing Sheets

(56)                    References Cited

U.S. PATENT DOCUMENTS

| | | | |
|---|---|---|---|
| 6,778,869 | B2 | 8/2004 | Champion |
| 7,130,608 | B2 | 10/2006 | Hollstrom et al. |
| 7,130,616 | B2 | 10/2006 | Janik |
| 7,143,939 | B2 | 12/2006 | Henzerling |
| 7,236,773 | B2 | 6/2007 | Thomas |
| 7,295,548 | B2 | 11/2007 | Blank et al. |
| 7,391,791 | B2 | 6/2008 | Balassanian et al. |
| 7,483,538 | B2 | 1/2009 | McCarty et al. |
| 7,571,014 | B1 | 8/2009 | Lambourne et al. |
| 7,630,501 | B2 | 12/2009 | Blank et al. |
| 7,643,894 | B2 | 1/2010 | Braithwaite et al. |
| 7,657,910 | B1 | 2/2010 | McAulay et al. |
| 7,853,341 | B2 | 12/2010 | McCarty et al. |
| 7,987,294 | B2 | 7/2011 | Bryce et al. |
| 8,014,423 | B2 | 9/2011 | Thaler et al. |
| 8,045,952 | B2 | 10/2011 | Qureshey et al. |
| 8,103,009 | B2 | 1/2012 | McCarty et al. |
| 8,234,395 | B2 | 7/2012 | Millington |
| 8,483,853 | B1 | 7/2013 | Lambourne |
| 8,942,252 | B2 | 1/2015 | Balassanian et al. |
| 10,220,109 | B2 * | 3/2019 | Becker ..................... A61L 9/00 |
| 2001/0042107 | A1 | 11/2001 | Palm |
| 2002/0022453 | A1 | 2/2002 | Balog et al. |
| 2002/0026442 | A1 | 2/2002 | Lipscomb et al. |
| 2002/0124097 | A1 | 9/2002 | Isely et al. |
| 2003/0157951 | A1 | 8/2003 | Hasty, Jr. |
| 2004/0024478 | A1 | 2/2004 | Hans et al. |
| 2007/0142944 | A1 | 6/2007 | Goldberg et al. |
| 2015/0297779 | A1 * | 10/2015 | Conroy ................. G08B 13/22 239/74 |
| 2016/0106875 | A1 * | 4/2016 | Chase .................... A61L 9/032 239/69 |

OTHER PUBLICATIONS

AudioTron Reference Manual, Version 3.0, May 2002, 70 pages.
AudioTron Setup Guide, Version 3.0, May 2002, 38 pages.

Bluetooth. "Specification of the Bluetooth System: The ad hoc SCATTERNET for affordable and highly functional wireless connectivity," Core, Version 1.0 A, Jul. 26, 1999, 1068 pages.
Bluetooth. "Specification of the Bluetooth System: Wireless connections made easy," Core, Version 1.0 B, Dec. 1, 1999, 1076 pages.
Dell, Inc. "Dell Digital Audio Receiver: Reference Guide," Jun. 2000, 70 pages.
Dell, Inc. "Start Here," Jun. 2000, 2 pages.
"Denon 2003-2004 Product Catalog," Denon, 2003-2004, 44 pages.
Jo et al., "Synchronized One-to-many Media Streaming with Adaptive Playout Control," Proceedings of SPIE, 2002, pp. 71-82, vol. 4861.
Jones, Stephen, "Dell Digital Audio Receiver: Digital upgrade for your analog stereo," Analog Stereo, Jun. 24, 2000 http://www.reviewsonline.com/articles/961906864.htm retrieved Jun. 18, 2014, 2 pages.
Louderback, Jim, "Affordable Audio Receiver Furnishes Homes With MP3," TechTV Vault. Jun. 28, 2000 retrieved Jul. 10, 2014, 2 pages.
Palm, Inc., "Handbook for the Palm VII Handheld," May 2000, 311 pages.
Presentations at WinHEC 2000, May 2000, 138 pages.
*Sonos, Inc.* v. *D&M Holdings* (No. 14-1330-RGA), DI 219, Claim Construction Opinion (Jan. 12, 2017) (24 pages).
U.S. Appl. No. 60/490,768, filed Jul. 28, 2003, entitled "Method for synchronizing audio playback between multiple networked devices," 13 pages.
U.S. Appl. No. 60/825,407, filed Sep. 12, 2006, entitled "Controlling and manipulating groupings in a multi-zone music or media system," 82 pages.
UPnP; "Universal Plug and Play Device Architecture," Jun. 8, 2000; version 1.0; Microsoft Corporation; pp. 1-54.
Yamaha DME 64 Owner's Manual; copyright 2004, 80 pages.
Yamaha DME Designer 3.5 setup manual guide; copyright 2004, 16 pages.
Yamaha DME Designer 3.5 User Manual; Copyright 2004, 507 pages.

* cited by examiner

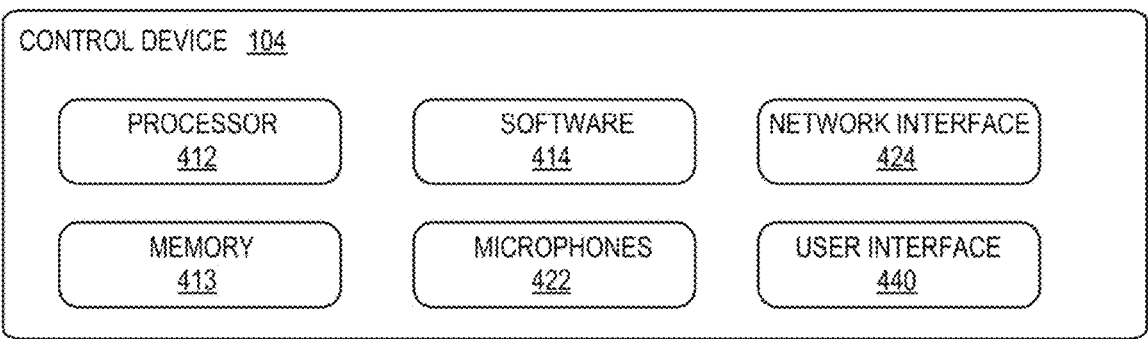

CONTROL DEVICE  104

| PROCESSOR 412 | SOFTWARE 414 | NETWORK INTERFACE 424 |

| MEMORY 413 | MICROPHONES 422 | USER INTERFACE 440 |

NOW PLAYING  (Office)

Track Title
Artist Name                                                544

QUEUE

Track 1
Track 2                                                      546
Track 3
Track 4

Music Source 1     First VAS
Music Source 2     Second VAS                                548
Music Source 3
+ ADD Music source   + ADD VAS source

🔊 ▭▭▭▭○▭▭▭▭▭▭▭                                              542

↻  ⊲⊲  ▷  ⊳⊳  ⇅
⤬

☆         ♫          🏠         🔍 ⊙               541
Sonos   Browse    Rooms    Search
                              music

📞  No Music
Balcony                          Group

↩  Audio Component
     *Living Room*
Living Room                      Group
                                              543

📞  No Music
Dining Room
+ Kitchen                        Group

📞  No Music
Office                           Group

⊲⊲      ▷      ⊳⊳

☆      ♫      🏠      🔍 ⊙
Sonos  Browse  Rooms  Search
                        music

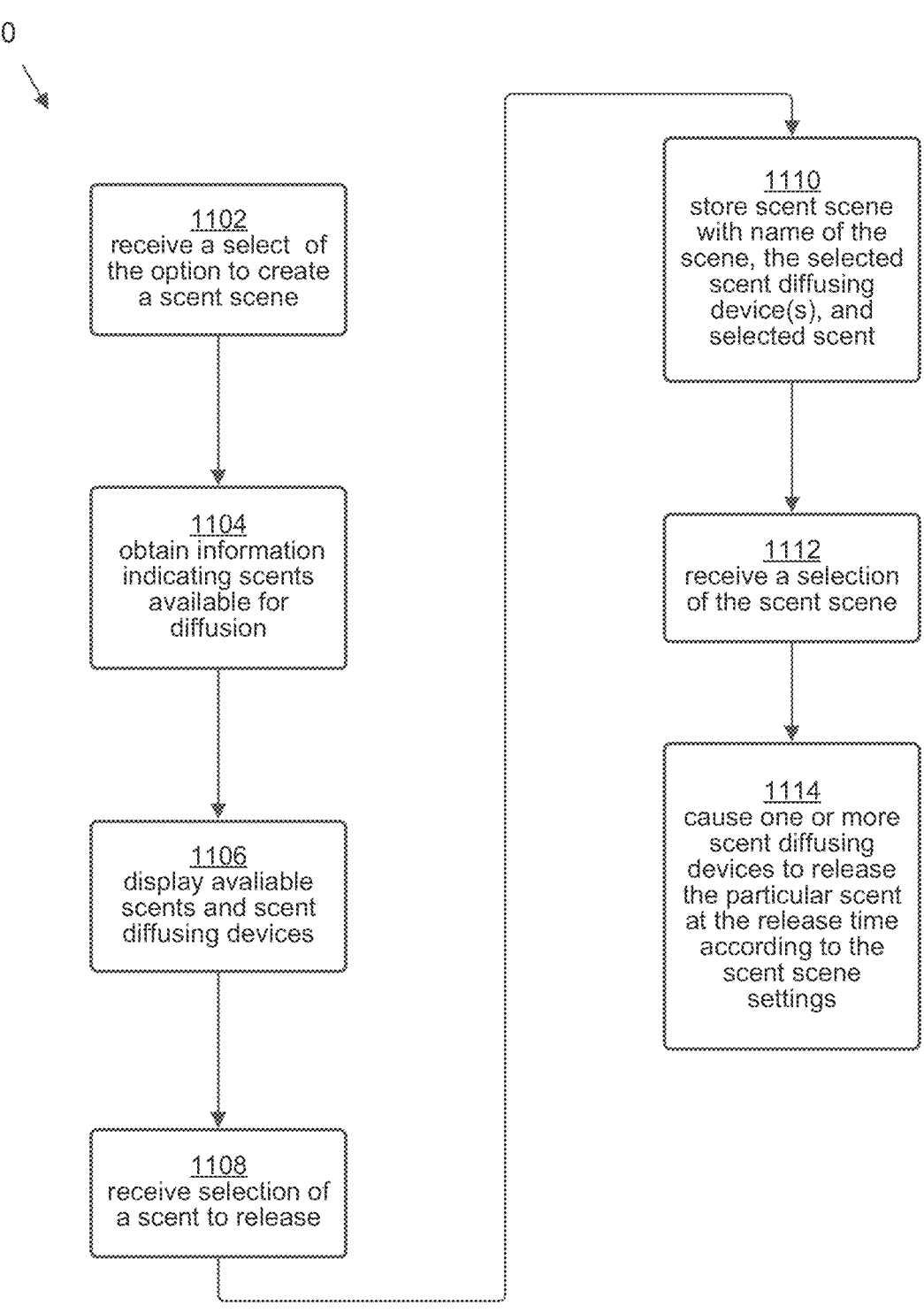

1102
receive a select of the option to create a scent scene

1104
obtain information indicating scents available for diffusion

1106
display avaliable scents and scent diffusing devices

1108
receive selection of a scent to release

1110
store scent scene with name of the scene, the selected scent diffusing device(s), and selected scent

1112
receive a selection of the scent scene

1114
cause one or more scent diffusing devices to release the particular scent at the release time according to the scent scene settings

*Fig. 11*

SCENT DIFFUSING SYSTEM

CROSS REFERENCE TO RELATED APPLICATIONS

This application claims the benefit under 35 U.S.C. § 119 of U.S. Provisional App. No. 63/298,887 filed on Jan. 12, 2022, which is incorporated herein by reference.

FIELD OF THE DISCLOSURE

The present technology relates to consumer goods and, more particularly, to methods, systems, products, features, services, and other elements directed to voice-assisted control of media playback systems or some aspect thereof.

BACKGROUND

Options for accessing and listening to digital audio in an out-loud setting were limited until in 2002, when SONOS, Inc. began development of a new type of playback system. Sonos then filed one of its first patent applications in 2003, entitled "Method for Synchronizing Audio Playback between Multiple Networked Devices," and began offering its first media playback systems for sale in 2005. The Sonos Wireless Home Sound System enables people to experience music from many sources via one or more networked playback devices. Through a software control application installed on a controller (e.g., smartphone, tablet, computer, voice input device), one can play what she wants in any room having a networked playback device. Media content (e.g., songs, podcasts, video sound) can be streamed to playback devices such that each room with a playback device can play back corresponding different media content. In addition, rooms can be grouped together for synchronous playback of the same media content, and/or the same media content can be heard in all rooms synchronously.

BRIEF DESCRIPTION OF THE DRAWINGS

Features, aspects, and advantages of the presently disclosed technology may be better understood with regard to the following description, appended claims, and accompanying drawings where:

Features, aspects, and advantages of the presently disclosed technology may be better understood with regard to the following description, appended claims, and accompanying drawings, as listed below. A person skilled in the relevant art will understand that the features shown in the drawings are for purposes of illustrations, and variations, including different and/or additional features and arrangements thereof, are possible.

FIG. 4 is a functional block diagram of an example controller device in accordance with aspects of the disclosure.

FIGS. 5A and 5B are controller interfaces in accordance with aspects of the disclosure.

FIG. 11 shows an example method of creating a scent scene.

Figure 1A:
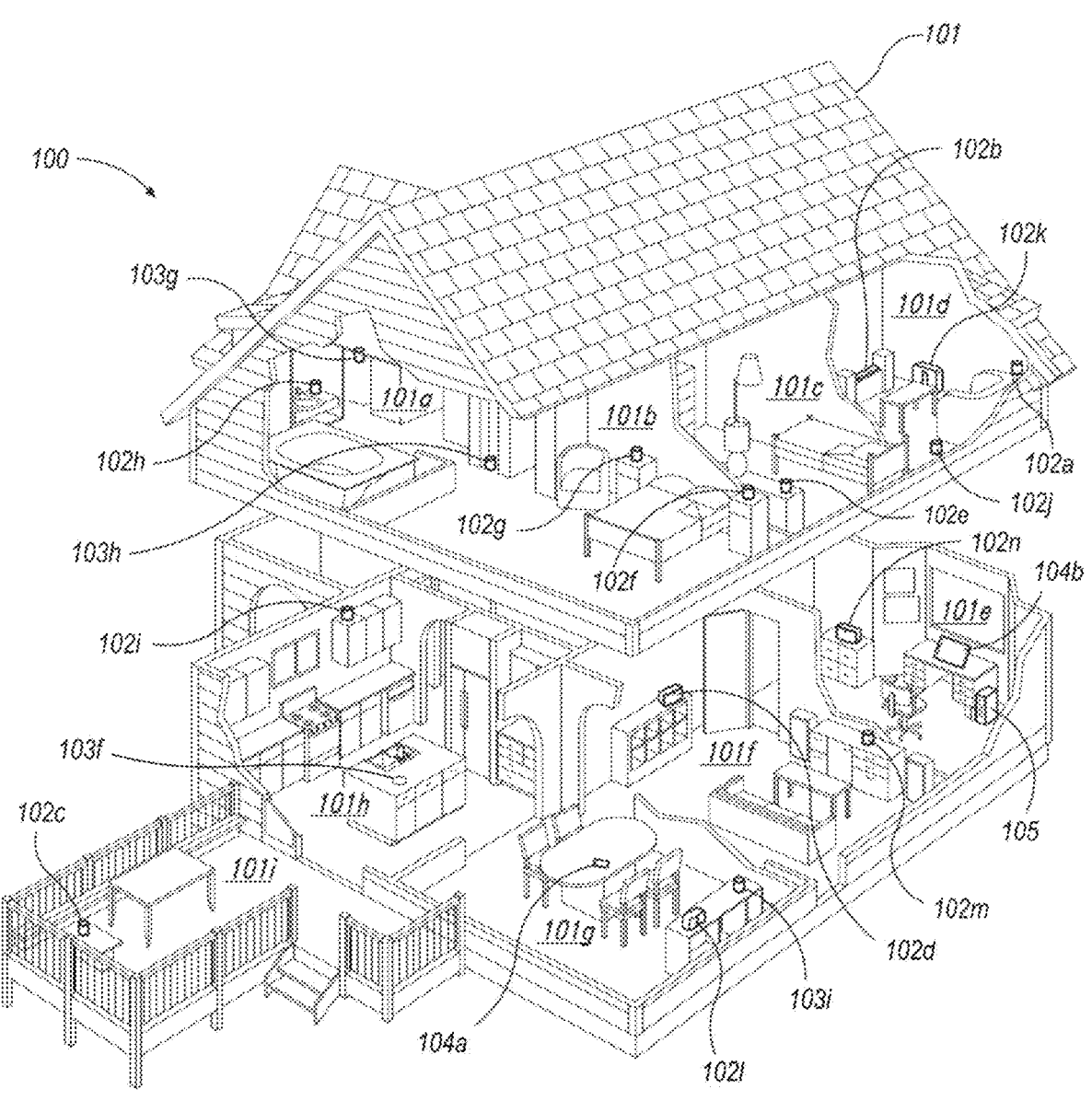
FIG. 1A is a partial cutaway view of an environment having a media playback system configured in accordance with aspects of the disclosed technology.

The drawings are for purposes of illustrating example embodiments, but it should be understood that the inventions are not limited to the arrangements and instrumentality shown in the drawings. In the drawings, identical reference numbers identify at least generally similar elements. To facilitate the discussion of any particular element, the most significant digit or digits of any reference number refers to the Figure in which that element is first introduced. For example, element 102$a$ is first introduced and discussed with reference to FIG. 1A.

DETAILED DESCRIPTION

I. Overview

Example techniques described herein involve a scent diffusing system. The system can include scent diffusing device(s), playback device(s), and controller device(s). The scent diffusing device can include a network interface enabling communication with other devices and systems and can include one or more canisters containing oils with different scents. The scent diffusing device can receive scent recipes developed by users and mix component oils based on the recipes. In some embodiments, scent scenes, quickstarts, or routines may be created for diffusion of particular scents by particular scent diffusing devices at a particular time.

The controller device may display on a graphical interface a representation of a first scent diffusing device and receive one or more inputs selecting the representation of the first scent diffusing device and a particular scent for the first scent diffusing device to release. At least one setting for the particular scent may be displayed which may include a scent release time. A selection of the at least one setting may be received, and the controller device may send a message to the first scent diffusing device including information indicating the scent to release and the selected at least one setting. The controller device can cause the first scent diffusing device to release the particular scent at the release time.

In some aspects, the at least one setting can further include a duration of scent release, a scent strength setting, or media content for playback setting including a playlist, radio station, or track for playback.

In another aspect, the controller device can be used to create a scent recipe. The device can receive and display canister information indicating one or more canisters containing scented oil for diffusion. The controller device can receive one or more inputs selecting a first canister and a second canister of the one or more canisters to include in a recipe for the particular scent and cause the recipe to be stored in a computing system remote to the controller device.

In another aspect, the controller device can be used to create a scent scene or set of routines.

While some embodiments described herein may refer to functions performed by given actors, such as "users" and/or other entities, it should be understood that this description is for purposes of explanation only. The claims should not be interpreted to require action by any such example actor unless explicitly required by the language of the claims themselves.

Moreover, some functions are described herein as being performed "based on" or "in response to" another element or function. "Based on" should be understood that one element or function is related to another function or element. "In response to" should be understood that one element or function is a necessary result of another function or element. For the sake of brevity, functions are generally described as being based on another function when a functional link exists; however, such disclosure should be understood as disclosing either type of functional relationship.

II. Example Operation Environment

Figure 1B:
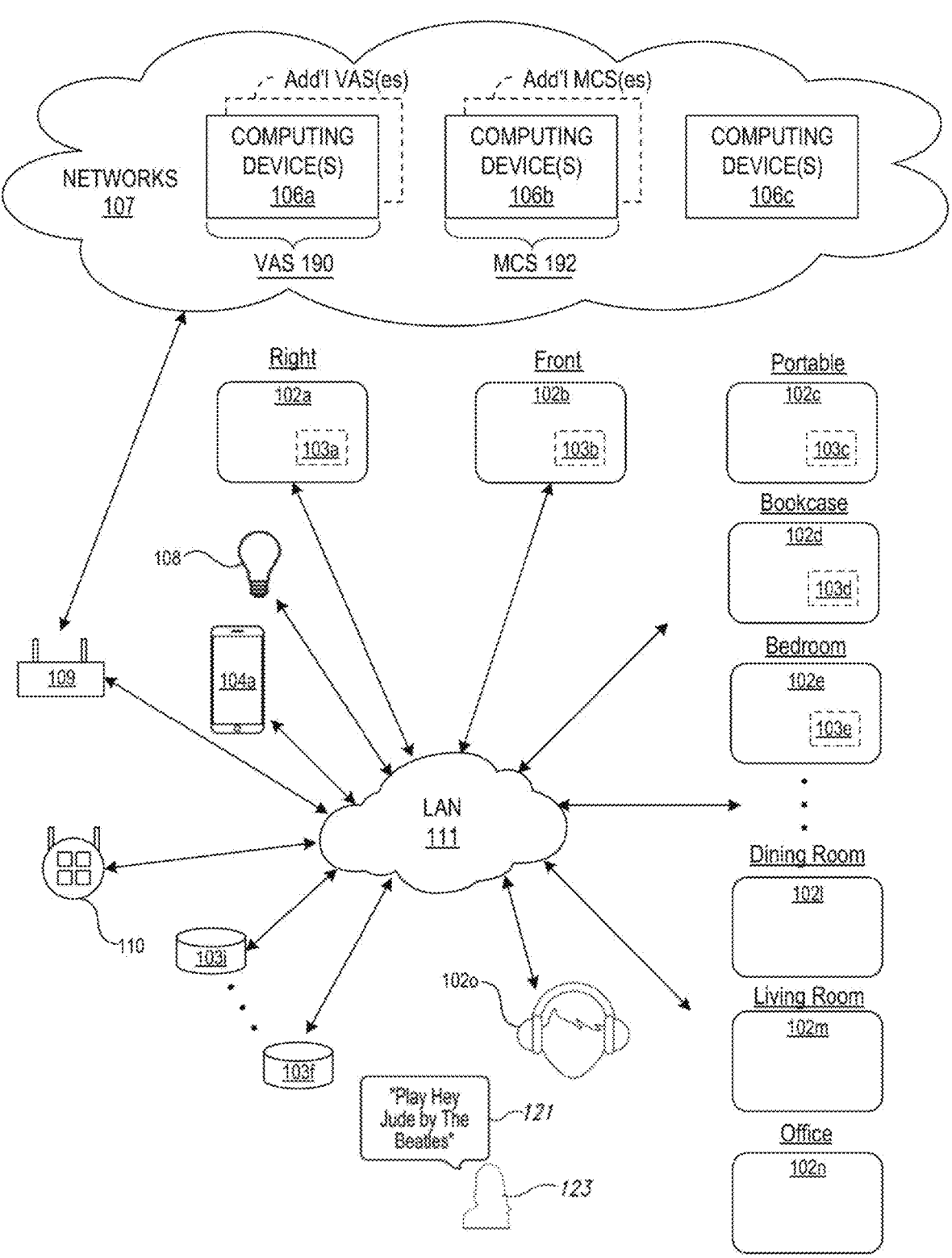
FIG. 1B is a schematic diagram of the media playback system of FIG. 1A and one or more networks.

FIGS. 1A and 1B illustrate an example configuration of a media playback system 100 (or "MPS 100") in which one or more embodiments disclosed herein may be implemented. Referring first to FIG. 1A, the MPS 100 as shown is associated with an example home environment having a plurality of rooms and spaces, which may be collectively referred to as a "home environment," "smart home," or "environment 101." The environment 101 comprises a household having several rooms, spaces, and/or playback zones, including a master bathroom 101*a*, a master bedroom 101*b*, (referred to herein as "Nick's Room"), a second bedroom 101*c*, a family room or den 101*d*, an office 101*e*, a living room 101*f*, a dining room 101*g*, a kitchen 101*h*, and an outdoor patio 101*i*. While certain embodiments and examples are described below in the context of a home environment, the technologies described herein may be implemented in other types of environments. In some embodiments, for example, the MPS 100 can be implemented in one or more commercial settings (e.g., a restaurant, mall, airport, hotel, a retail or other store), one or more vehicles (e.g., a sports utility vehicle, bus, car, a ship, a boat, an airplane), multiple environments (e.g., a combination of home and vehicle environments), and/or another suitable environment where multi-zone audio may be desirable.

Within these rooms and spaces, the MPS 100 includes one or more computing devices. Referring to FIGS. 1A and 1B together, such computing devices can include playback devices 102 (identified individually as playback devices 102*a*-102*n*), network microphone devices 103 (identified individually as "NMDs" 103*a*-102*i*), and controller devices 104*a* and 104*b* (collectively "controller devices 104"). Referring to FIG. 1B, the home environment may include additional and/or other computing devices, including local network devices, such as one or more smart illumination devices 108 (FIG. 1B), a smart thermostat 110, and a local computing device 105 (FIG. 1A).

With reference still to FIG. 1B, the various playback, network microphone, and controller devices 102, 103, and 104 and/or other network devices of the MPS 100 may be coupled to one another via point-to-point connections and/or over other connections, which may be wired and/or wireless, via a network 111, such as a LAN including a network router 109. For example, the playback device 102*j* in the Den 101*d* (FIG. 1A), which may be designated as the "Left" device, may have a point-to-point connection with the playback device 102*a*, which is also in the Den 101*d* and may be designated as the "Right" device. In a related embodiment, the Left playback device 102*j* may communicate with other network devices, such as the playback device 102*b*, which may be designated as the "Front" device, via a point-to-point connection and/or other connections via the NETWORK 111.

As further shown in FIG. 1B, the MPS 100 may be coupled to one or more remote computing devices 106 via a wide area network ("WAN") (i.e., the Internet), labeled here as the networks 107. In some embodiments, each remote computing device 106 may take the form of one or more cloud servers. The remote computing devices 106 may be configured to interact with computing devices in the environment 101 in various ways. For example, the remote computing devices 106 may be configured to facilitate streaming and/or controlling playback of media content, such as audio, in the home environment 101.

In some implementations, the various playback devices, NMDs, and/or controller devices 102-104 may be communicatively coupled to at least one remote computing device associated with a VAS and at least one remote computing device associated with a media content service ("MCS"). For instance, in the illustrated example of FIG. 1B, remote computing devices 106 are associated with a VAS 190 and remote computing devices 106*b* are associated with an MCS 192. Although only a single VAS 190 and a single MCS 192 are shown in the example of FIG. 1B for purposes of clarity, the MPS 100 may be coupled to multiple, different VASes and/or MCSes. In some implementations, VASes may be operated by one or more of AMAZON, GOOGLE, APPLE, MICROSOFT, SONOS or other voice assistant providers. In some implementations, MCSes may be operated by one or more of SPOTIFY, PANDORA, AMAZON MUSIC, or other media content services. Media content services are also referred to herein as streaming audio services.

As further shown in FIG. 1B, the remote computing devices 106 further include remote computing device 106*c* configured to perform certain operations, such as remotely facilitating media playback functions, managing device and system status information, directing communications between the devices of the MPS 100 and one or multiple VASes and/or MCSes, among other operations. In one example, the remote computing devices 106*c* provide cloud servers for one or more SONOS Wireless HiFi Systems.

In various implementations, one or more of the playback devices 102 may take the form of or include an on-board (e.g., integrated) network microphone device. For example, the playback devices 102*a*-*e* include or are otherwise equipped with corresponding NMDs 103*a*-*e*, respectively. A playback device that includes or is equipped with an NMD may be referred to herein interchangeably as a playback device or an NMD unless indicated otherwise in the description. In some cases, one or more of the NMDs 103 may be a stand-alone device. For example, the NMDs 103*f* and 103*g* may be stand-alone devices. A stand-alone NMD may omit components and/or functionality that is typically included in a playback device, such as a speaker or related electronics. For instance, in such cases, a stand-alone NMD may not produce audio output or may produce limited audio output (e.g., relatively low-quality audio output).

The various playback and network microphone devices 102 and 103 of the MPS 100 may each be associated with a unique name, which may be assigned to the respective devices by a user, such as during setup of one or more of these devices. For instance, as shown in the illustrated example of FIG. 1B, a user may assign the name "Bookcase" to playback device 102*d* because it is physically situated on a bookcase. Similarly, the NMD 103*f* may be assigned the named "Island" because it is physically situated on an island countertop in the kitchen 101*h* (FIG. 1A). Some playback devices may be assigned names according to a zone or room, such as the playback devices 102*e*, 102*l*, 102*m*, and 102*n*, which are named "Bedroom," "Dining Room," "Living Room," and "Office," respectively. Further, certain playback devices may have functionally descriptive names. For example, the playback devices 102*a* and 102*b* are assigned the names "Right" and "Front," respectively, because these two devices are configured to provide specific audio channels during media playback in the zone of the Den 101*d* (FIG. 1A). The playback device 102*c* in the Patio may be named portable because it is battery-powered and/or readily transportable to different areas of the environment 101. Other naming conventions are possible.

As discussed above, an NMD may detect and process sound from its environment, such as sound that includes background noise mixed with speech spoken by a person in the NMD's vicinity. For example, as sounds are detected by the NMD in the environment, the NMD may process the detected sound to determine if the sound includes speech that contains voice input intended for the NMD and ultimately a particular VAS. For example, the NMD may identify whether speech includes a wake word associated with a particular VAS.

In the illustrated example of FIG. 1B, the NMDs 103 are configured to interact with the VAS 190 over a network via the network 111 and the router 109. Interactions with the VAS 190 may be initiated, for example, when an NMD identifies in the detected sound a potential wake word. The identification causes a wake-word event, which in turn causes the NMD to begin transmitting detected-sound data to the VAS 190. In some implementations, the various local network devices 102-105 (FIG. 1A) and/or remote computing devices 106*c* of the MPS 100 may exchange various feedback, information, instructions, and/or related data with the remote computing devices associated with the selected VAS. Such exchanges may be related to or independent of transmitted messages containing voice inputs. In some embodiments, the remote computing device(s) and the MPS 100 may exchange data via communication paths as described herein and/or using a metadata exchange channel as described in U.S. application Ser. No. 15/438,749 filed Feb. 21, 2017, and titled "Voice Control of a Media Playback System," which is herein incorporated by reference in its entirety.

Upon receiving the stream of sound data, the VAS 190 determines if there is voice input in the streamed data from the NMD, and if so the VAS 190 will also determine an underlying intent in the voice input. The VAS 190 may next transmit a response back to the MPS 100, which can include transmitting the response directly to the NMD that caused the wake-word event. The response is typically based on the intent that the VAS 190 determined was present in the voice input. As an example, in response to the VAS 190 receiving a voice input with an utterance to "Play Hey Jude by The Beatles," the VAS 190 may determine that the underlying intent of the voice input is to initiate playback and further determine that intent of the voice input is to play the particular song "Hey Jude." After these determinations, the VAS 190 may transmit a command to a particular MCS 192 to retrieve content (i.e., the song "Hey Jude"), and that MCS 192, in turn, provides (e.g., streams) this content directly to the MPS 100 or indirectly via the VAS 190. In some implementations, the VAS 190 may transmit to the MPS 100 a command that causes the MPS 100 itself to retrieve the content from the MCS 192.

In certain implementations, NMDs may facilitate arbitration amongst one another when voice input is identified in speech detected by two or more NMDs located within proximity of one another. For example, the NMD-equipped playback device 102*d* in the environment 101 (FIG. 1A) is in relatively close proximity to the NMD-equipped Living Room playback device 102*m*, and both devices 102*d* and 102*m* may at least sometimes detect the same sound. In such cases, this may require arbitration as to which device is ultimately responsible for providing detected-sound data to the remote VAS. Examples of arbitrating between NMDs may be found, for example, in previously referenced U.S. application Ser. No. 15/438,749.

In certain implementations, an NMD may be assigned to, or otherwise associated with, a designated or default playback device that may not include an NMD. For example, the Island NMD 103*f* in the kitchen 101*h* (FIG. 1A) may be assigned to the dining room playback device 102*l*, which is in relatively close proximity to the Island NMD 103*f*. In practice, an NMD may direct an assigned playback device to play audio in response to a remote VAS receiving a voice input from the NMD to play the audio, which the NMD might have sent to the VAS in response to a user speaking a command to play a certain song, album, playlist, etc. Additional details regarding assigning NMDs and playback devices as designated or default devices may be found, for example, in previously referenced U.S. Patent Application No.

Further aspects relating to the different components of the example MPS 100 and how the different components may interact to provide a user with a media experience may be found in the following sections. While discussions herein may generally refer to the example MPS 100, technologies described herein are not limited to applications within, among other things, the home environment described above. For instance, the technologies described herein may be useful in other home environment configurations comprising more or fewer of any of the playback, network microphone, and/or controller devices 102-104. For example, the technologies herein may be utilized within an environment having a single playback device 102 and/or a single NMD 103. In some examples of such cases, the NETWORK 111 (FIG. 1B) may be eliminated and the single playback device 102 and/or the single NMD 103 may communicate directly with the remote computing devices 106-*d*. In some embodiments, a telecommunication network (e.g., an LTE network, a 5G network, etc.) may communicate with the various playback, network microphone, and/or controller devices 102-104 independent of a LAN.

a. Example Playback & Network Microphone Devices

Figure 2A:
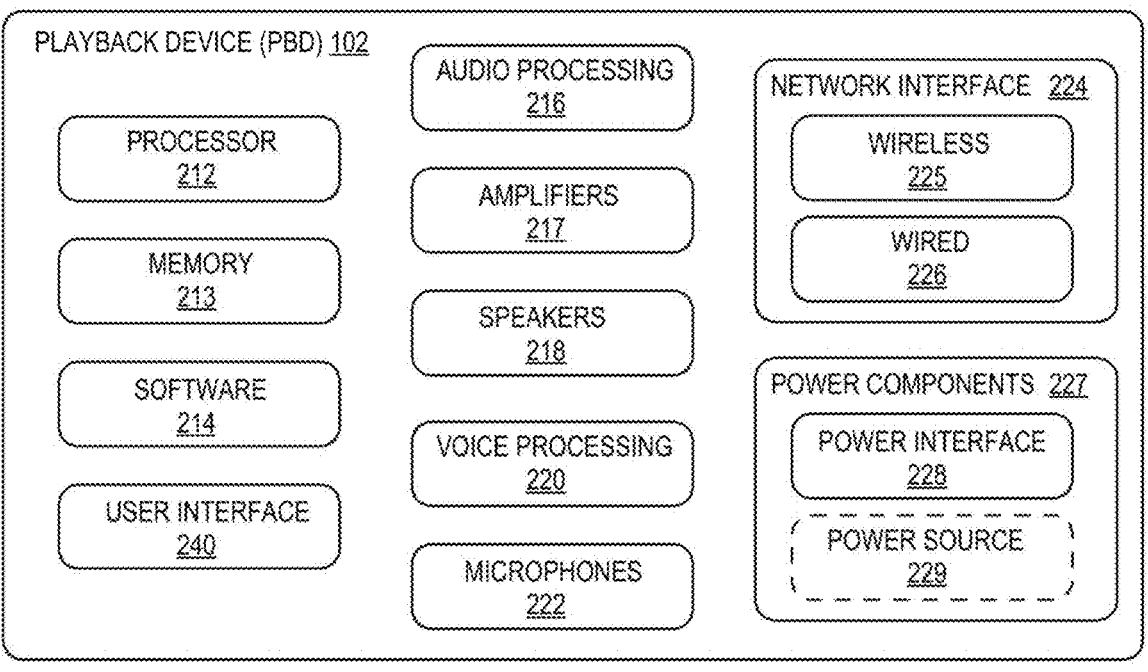
FIG. 2A is a functional block diagram of an example playback device.

FIG. 2A is a functional block diagram illustrating certain aspects of one of the playback devices 102 of the MPS 100 of FIGS. 1A and 1B. As shown, the playback device 102 includes various components, each of which is discussed in further detail below, and the various components of the playback device 102 may be operably coupled to one another via a system bus, communication network, or some other connection mechanism. In the illustrated example of FIG. 2A, the playback device 102 may be referred to as an "NMD-equipped" playback device because it includes components that support the functionality of an NMD, such as one of the NMDs 103 shown in FIG. 1A.

As shown, the playback device 102 includes at least one processor 212, which may be a clock-driven computing component configured to process input data according to instructions stored in memory 213. The memory 213 may be a tangible, non-transitory, computer-readable medium configured to store instructions that are executable by the processor 212. For example, the memory 213 may be data storage that can be loaded with software code 214 that is executable by the processor 212 to achieve certain functions.

In one example, these functions may involve the playback device 102 retrieving audio data from an audio source, which may be another playback device. In another example, the functions may involve the playback device 102 sending audio data, detected-sound data (e.g., corresponding to a voice input), and/or other information to another device on a network via at least one network interface 224. In yet another example, the functions may involve the playback device 102 causing one or more other playback devices to synchronously playback audio with the playback device 102. In yet a further example, the functions may involve the playback device 102 facilitating being paired or otherwise bonded with one or more other playback devices to create a multi-channel audio environment. Numerous other example functions are possible, some of which are discussed below.

As just mentioned, certain functions may involve the playback device 102 synchronizing playback of audio content with one or more other playback devices. During synchronous playback, a listener may not perceive time-delay differences between playback of the audio content by the synchronized playback devices. U.S. Pat. No. 8,234,395 filed on Apr. 4, 2004, and titled "System and method for synchronizing operations among a plurality of independently clocked digital data processing devices," which is hereby incorporated by reference in its entirety, provides in more detail some examples for audio playback synchronization among playback devices.

To facilitate audio playback, the playback device 102 includes audio processing components 216 that are generally configured to process audio prior to the playback device 102 rendering the audio. In this respect, the audio processing components 216 may include one or more digital-to-analog converters ("DAC"), one or more audio preprocessing components, one or more audio enhancement components, one or more digital signal processors ("DSPs"), and so on. In some implementations, one or more of the audio processing components 216 may be a subcomponent of the processor 212. In operation, the audio processing components 216 receive analog and/or digital audio and process and/or otherwise intentionally alter the audio to produce audio signals for playback.

The produced audio signals may then be provided to one or more audio amplifiers 217 for amplification and playback through one or more speakers 218 operably coupled to the amplifiers 217. The audio amplifiers 217 may include components configured to amplify audio signals to a level for driving one or more of the speakers 218.

In another aspect, the software code 214 configures the playback device 102 to be operable in a plurality of non contemporary room sound modes. In each mode, the playback device 102 may adopt certain settings and/or configurations in accordance with the room sound mode. Further, the software code 214 may be configured to detect occurrence of various triggers corresponding to one of more of the room sounds, and responsively switch the first playback device from operating in one mode to operating in another mode. Further details related to the room sound modes are described in connection with section III below.

Each of the speakers 218 may include an individual transducer (e.g., a "driver") or the speakers 218 may include a complete speaker system involving an enclosure with one or more drivers. A particular driver of a speaker 218 may include, for example, a subwoofer (e.g., for low frequencies), a mid-range driver (e.g., for middle frequencies), and/or a tweeter (e.g., for high frequencies). In some cases, a transducer may be driven by an individual corresponding audio amplifier of the audio amplifiers 217. In some implementations, a playback device may not include the speakers 218, but instead may include a speaker interface for connecting the playback device to external speakers. In certain embodiments, a playback device may include neither the speakers 218 nor the audio amplifiers 217, but instead may include an audio interface (not shown) for connecting the playback device to an external audio amplifier or audio-visual receiver.

In addition to producing audio signals for playback by the playback device 102, the audio processing components 216 may be configured to process audio to be sent to one or more other playback devices, via the network interface 224, for playback. In example scenarios, audio content to be processed and/or played back by the playback device 102 may be received from an external source, such as via an audio line-in interface (e.g., an auto-detecting 3.5 mm audio line-in connection) of the playback device 102 (not shown) or via the network interface 224, as described below.

As shown, the at least one network interface 224, may take the form of one or more wireless interfaces 225 and/or one or more wired interfaces 226. A wireless interface may provide network interface functions for the playback device 102 to wirelessly communicate with other devices (e.g., other playback device(s), NMD(s), and/or controller device(s)) in accordance with a communication protocol (e.g., any wireless standard including IEEE 802.11a, 802.11b, 802.11g, 802.11n, 802.11ac, 802.15, 4G mobile communication standard, and so on). A wired interface may provide network interface functions for the playback device 102 to communicate over a wired connection with other devices in accordance with a communication protocol (e.g., IEEE 802.3). While the network interface 224 shown in FIG. 2A include both wired and wireless interfaces, the playback device 102 may in some implementations include only wireless interface(s) or only wired interface(s).

In general, the network interface 224 facilitates data flow between the playback device 102 and one or more other devices on a data network. For instance, the playback device 102 may be configured to receive audio content over the data network from one or more other playback devices, network devices within a LAN, and/or audio content sources over a WAN, such as the Internet. In one example, the audio content and other signals transmitted and received by the playback device 102 may be transmitted in the form of digital packet data comprising an Internet Protocol (IP)-based source address and IP-based destination addresses. In such a case, the network interface 224 may be configured to parse the digital packet data such that the data destined for the playback device 102 is properly received and processed by the playback device 102.

As shown in FIG. 2A, the playback device 102 also includes voice processing components 220 that are operably coupled to one or more microphones 222. The microphones 222 are configured to detect sound (i.e., acoustic waves) in the environment of the playback device 102, which is then provided to the voice processing components 220. More specifically, each microphone 222 is configured to detect sound and convert the sound into a digital or analog signal representative of the detected sound, which can then cause the voice processing component 220 to perform various functions based on the detected sound, as described in greater detail below. In one implementation, the microphones 222 are arranged as an array of microphones (e.g., an array of six microphones). In some implementations, the playback device 102 includes more than six microphones (e.g., eight microphones or twelve microphones) or fewer than six microphones (e.g., four microphones, two microphones, or a single microphones).

In operation, the voice-processing components 220 are generally configured to detect and process sound received via the microphones 222, identify potential voice input in the detected sound, and extract detected-sound data to enable a VAS, such as the VAS 190 (FIG. 1B), to process voice input identified in the detected-sound data. The voice processing components 220 may include one or more analog-to-digital converters, an acoustic echo canceller ("AEC"), a spatial processor (e.g., one or more multi-channel Wiener filters, one or more other filters, and/or one or more beam former components), one or more buffers (e.g., one or more circular buffers), one or more wake-word engines, one or more voice extractors, and/or one or more speech processing components (e.g., components configured to recognize a voice of a particular user or a particular set of users associated with a household), among other example voice processing components. In example implementations, the voice processing components 220 may include or otherwise take the form of one or more DSPs or one or more modules of a DSP. In this respect, certain voice processing components 220 may be configured with particular parameters (e.g., gain and/or spectral parameters) that may be modified or otherwise tuned to achieve particular functions. In some implementations, one or more of the voice processing components 220 may be a subcomponent of the processor 212.

As further shown in FIG. 2A, the playback device 102 also includes power components 227. The power components 227 include at least an external power source interface 228, which may be coupled to a power source (not shown) via a power cable or the like that physically connects the playback device 102 to an electrical outlet or some other external power source. Other power components may include, for example, transformers, converters, and like components configured to format electrical power.

In some implementations, the power components 227 of the playback device 102 may additionally include an internal power source 229 (e.g., one or more batteries) configured to power the playback device 102 without a physical connection to an external power source. When equipped with the internal power source 229, the playback device 102 may operate independent of an external power source. In some such implementations, the external power source interface 228 may be configured to facilitate charging the internal power source 229. As discussed before, a playback device comprising an internal power source may be referred to herein as a "portable playback device." On the other hand, a playback device that operates using an external power source may be referred to herein as a "stationary playback device," although such a device may in fact be moved around a home or other environment.

The playback device 102 further includes a user interface 240 that may facilitate user interactions independent of or in conjunction with user interactions facilitated by one or more of the controller devices 104. In various embodiments, the user interface 240 includes one or more physical buttons and/or supports graphical interfaces provided on touch sensitive screen(s) and/or surface(s), among other possibilities, for a user to directly provide input. The user interface 240 may further include one or more of lights (e.g., LEDs) and the speakers to provide visual and/or audio feedback to a user.

Figure 2B:
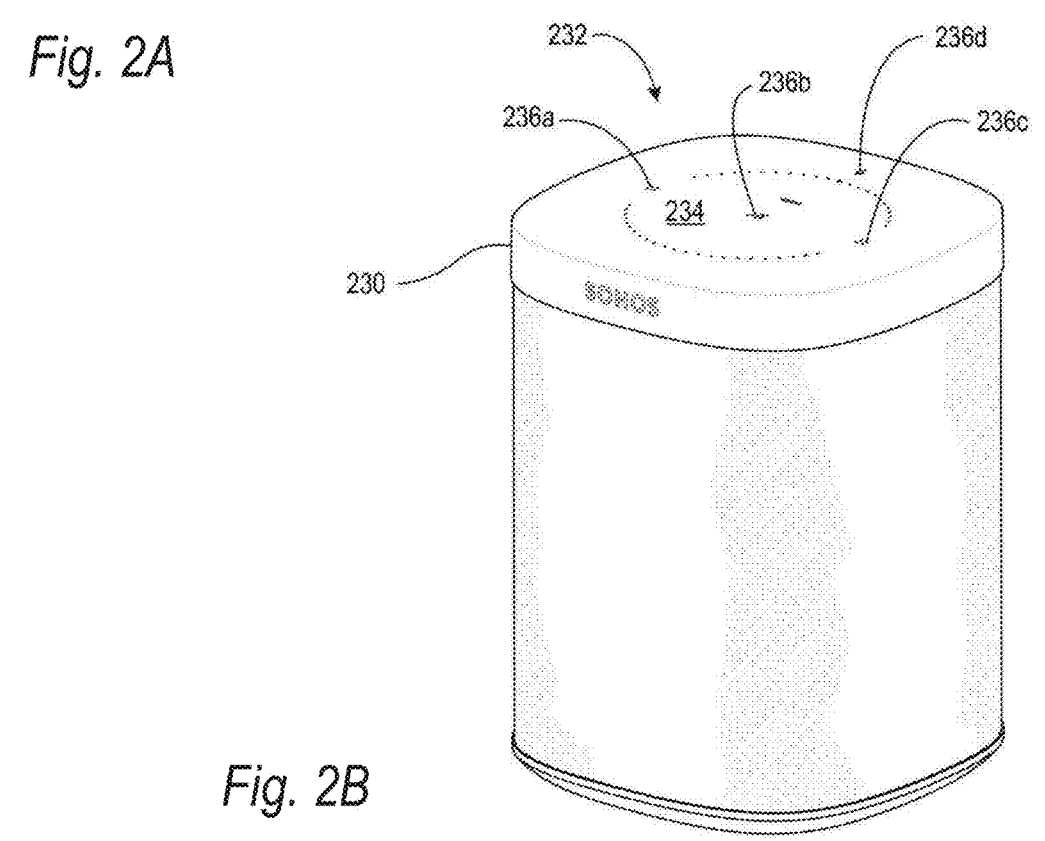
FIG. 2B is an isometric diagram of an example housing of the playback device of FIG. 2A.

As an illustrative example, FIG. 2B shows an example housing 230 of the playback device 102 that includes a user interface in the form of a control area 232 at a top portion 234 of the housing 230. The control area 232 includes buttons 236a-c for controlling audio playback, volume level, and other functions. The control area 232 also includes a button 236d for toggling the microphones 222 to either an on state or an off state.

As further shown in FIG. 2B, the control area 232 is at least partially surrounded by apertures formed in the top portion 234 of the housing 230 through which the microphones 222 (not visible in FIG. 2B) receive the sound in the environment of the playback device 102. The microphones 222 may be arranged in various positions along and/or within the top portion 234 or other areas of the housing 230 so as to detect sound from one or more directions relative to the playback device 102.

By way of illustration, SONOS, Inc. presently offers (or has offered) for sale certain playback devices that may implement certain of the embodiments disclosed herein, including a "PLAY:1," "PLAY:3," "PLAY:5," "PLAYBAR," "CONNECT:AMP," "PLAYBASE," "BEAM," "CONNECT," and "SUB." Any other past, present, and/or future playback devices may additionally or alternatively be used to implement the playback devices of example embodiments disclosed herein. Additionally, it should be understood that a playback device is not limited to the examples illustrated in FIG. 2A or 2B or to the SONOS product offerings. For example, a playback device may include, or otherwise take the form of, a wired or wireless headphone set, which may operate as a part of the MPS 100 via a network interface or the like. In another example, a playback device may include or interact with a docking station for personal mobile media playback devices. In yet another example, a playback device may be integral to another device or component such as a television, a lighting fixture, or some other device for indoor or outdoor use.

Figure 2C:
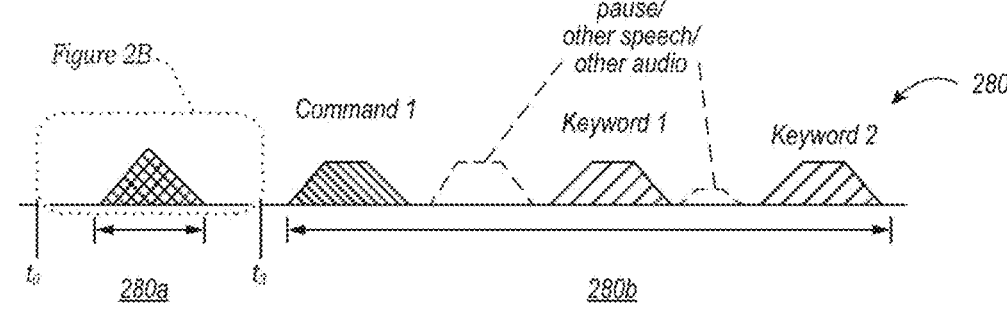
FIG. 2C is a diagram of an example voice input.

FIG. 2C is a diagram of an example voice input 280 that may be processed by an NMD or an NMD-equipped playback device. The voice input 280 may include a keyword portion 280a and an utterance portion 280b. The keyword portion 280a may include a wake word or a command keyword. In the case of a wake word, the keyword portion 280a corresponds to detected sound that caused a wake-word The utterance portion 280b corresponds to detected sound that potentially comprises a user request following the keyword portion 280a. An utterance portion 280b can be processed to identify the presence of any words in detected-sound data by the NMD in response to the event caused by the keyword portion 280a. In various implementations, an underlying intent can be determined based on the words in the utterance portion 280b. In certain implementations, an underlying intent can also be based or at least partially based on certain words in the keyword portion 280a, such as when keyword portion includes a command keyword. In any case, the words may correspond to one or more commands, as well as a certain command and certain keywords. A keyword in the voice utterance portion 280b may be, for example, a word identifying a particular device or group in the MPS 100. For instance, in the illustrated example, the keywords in the voice utterance portion 280b may be one or more words identifying one or more zones in which the music is to be played, such as the Living Room and the Dining Room (FIG. 1A). In some cases, the utterance portion 280b may include additional information, such as detected pauses (e.g., periods of non-speech) between words spoken by a user, as shown in FIG. 2C. The pauses may demarcate the locations of separate commands, keywords, or other information spoke by the user within the utterance portion 280b.

Based on certain command criteria, the NMD and/or a remote VAS may take actions as a result of identifying one or more commands in the voice input. Command criteria may be based on the inclusion of certain keywords within the voice input, among other possibilities. Additionally, or alternatively, command criteria for commands may involve identification of one or more control-state and/or zone-state variables in conjunction with identification of one or more particular commands. Control-state variables may include, for example, indicators identifying a level of volume, a queue associated with one or more devices, and playback state, such as whether devices are playing a queue, paused, etc. Zone-state variables may include, for example, indicators identifying which, if any, zone players are grouped.

In some implementations, the MPS 100 is configured to temporarily reduce the volume of audio content that it is playing upon detecting a certain keyword, such as a wake word, in the keyword portion 280a. The MPS 100 may restore the volume after processing the voice input 280. Such a process can be referred to as ducking, examples of which are disclosed in U.S. patent application Ser. No. 15/438,749, incorporated by reference herein in its entirety.

Figure 2D:
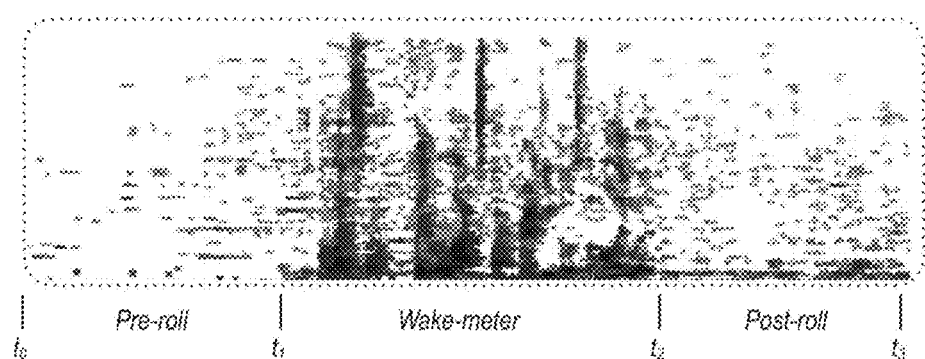
FIG. 2D is a graph depicting an example sound specimen in accordance with aspects of the disclosure.

FIG. 2D shows an example sound specimen. In this example, the sound specimen corresponds to the sound-data stream (e.g., one or more audio frames) associated with a spotted wake word or command keyword in the keyword portion 280a of FIG. 2A. As illustrated, the example sound specimen comprises sound detected in an NMD's environment (i) immediately before a wake or command word was spoken, which may be referred to as a pre-roll portion (between times to and $t_1$), (ii) while a wake or command word was spoken, which may be referred to as a wake-meter portion (between times $t_1$ and $t_2$), and/or (iii) after the wake or command word was spoken, which may be referred to as a post-roll portion (between times $t_2$ and $t_3$). Other sound specimens are also possible. In various implementations, aspects of the sound specimen can be evaluated according to an acoustic model which aims to map spectral features to phonemes in a given language model for further processing. For example, automatic speech recognition (ASR) may include such mapping for command-keyword detection. Wake-word detection engines, by contrast, may be precisely tuned to identify a specific wake-word, and a downstream action of invoking a VAS (e.g., by targeting only nonce words in the voice input processed by the playback device).

ASR for command keyword detection may be tuned to accommodate a wide range of keywords (e.g., 5, 10, 100, 1,000, 10,000 keywords). Command keyword detection, in contrast to wake-word detection, may involve feeding ASR output to an onboard, local NLU which together with the ASR determine when command word events have occurred. In some implementations described below, the local NLU may determine an intent based on one or more other keywords in the ASR output produced by a particular voice input. In these or other implementations, a playback device may act on a detected command keyword event only when the playback devices determines that certain conditions have been met, such as environmental conditions (e.g., low background noise).

The playback device 102 may further include a voice activity detector (VAD), which may be implemented as part of the voice processing components 220. The VAD is configured to detect the presence (or lack thereof) of voice activity in the sound-data stream from the microphones 222. In particular, the VAD may analyze frames corresponding to the pre-roll portion of the voice input 280a (FIG. 2D) with one or more voice detection algorithms to determine whether voice activity was present in the environment in certain time windows prior to a keyword portion of the voice input 280a.

The VAD may utilize any suitable voice activity detection algorithms. Example voice detection algorithms involve determining whether a given frame includes one or more features or qualities that correspond to voice activity, and further determining whether those features or qualities diverge from noise to a given extent (e.g., if a value exceeds a threshold for a given frame). Some example voice detection algorithms involve filtering or otherwise reducing noise in the frames prior to identifying the features or qualities.

In some examples, the VAD may determine whether voice activity is present in the environment based on one or more metrics. For example, the VAD can be configured to distinguish between frames that include voice activity and frames that don't include voice activity. The frames that the VAD determines have voice activity may be caused by speech regardless of whether it near- or far-field. In this example and others, the VAD may determine a count of frames in the voice input 280a that indicate voice activity. If this count exceeds a threshold percentage or number of frames, the VAD may be configured to output a signal or set a state variable indicating that voice activity is present in the environment. Other metrics may be used as well in addition to, or as an alternative to, such a count.

When the VAD detects voice activity in an environment, the VAD may set a state variable in the playback device indicating that voice activity is present. Conversely, when the VAD does not voice activity in an environment, the VAD may set the state variable in the playback device to indicate that voice activity is not present. Changing the state of this state variable may function as a mode trigger condition in some examples.

b. Example Playback Device Configurations

Figures 3A, 3B, 3C, 3D, 3E:
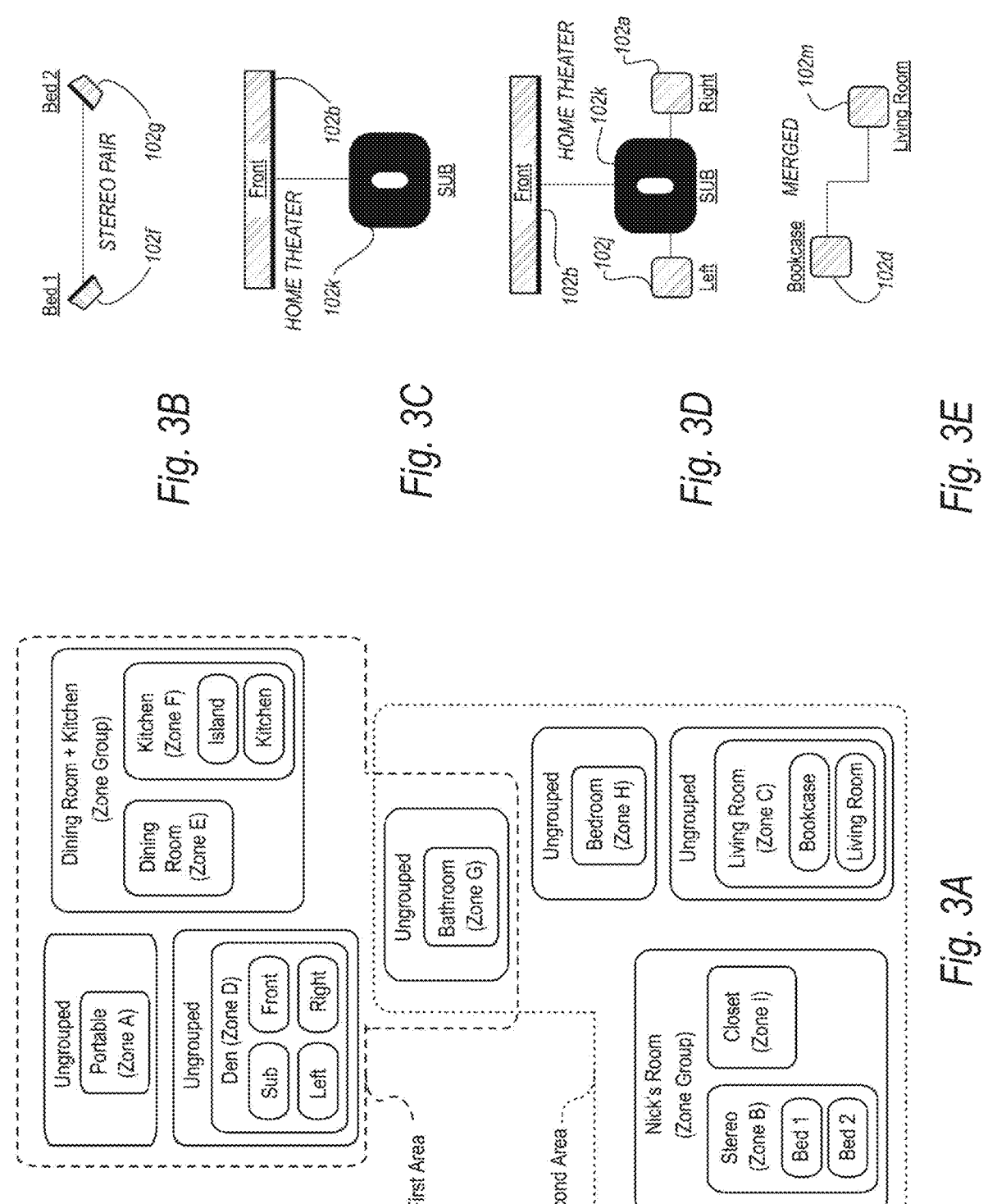
FIGS. 3A, 3B, 3C, 3D and 3E are diagrams showing example playback device configurations in accordance with aspects of the disclosure.

FIGS. 3A-3E show example configurations of playback devices. Referring first to FIG. 3A, in some example instances, a single playback device may belong to a zone. For example, the playback device 102c (FIG. 1A) on the Patio may belong to Zone A. In some implementations described below, multiple playback devices may be "bonded" to form a "bonded pair," which together form a single zone. For example, the playback device 102f (FIG. 1A) named "Bed 1" in FIG. 3A may be bonded to the playback device 102g (FIG. 1A) named "Bed 2" in FIG. 3A to form Zone B. Bonded playback devices may have different playback responsibilities (e.g., channel responsibilities). In another implementation described below, multiple playback devices may be merged to form a single zone. For example, the playback device 102d named "Bookcase" may be merged with the playback device 102m named "Living Room" to form a single Zone C. The merged playback devices 102d and 102m may not be specifically assigned different playback responsibilities. That is, the merged playback devices 102*d* and 102*m* may, aside from playing audio content in synchrony, each play audio content as they would if they were not merged.

For purposes of control, each zone in the MPS 100 may be represented as a single user interface ("UI") entity. For example, as displayed by the controller devices 104, Zone A may be provided as a single entity named "Portable," Zone B may be provided as a single entity named "Stereo," and Zone C may be provided as a single entity named "Living Room."

In various embodiments, a zone may take on the name of one of the playback devices belonging to the zone. For example, Zone C may take on the name of the Living Room device 102*m* (as shown). In another example, Zone C may instead take on the name of the Bookcase device 102*d*. In a further example, Zone C may take on a name that is some combination of the Bookcase device 102*d* and Living Room device 102*m*. The name that is chosen may be selected by a user via inputs at a controller device 104. In some embodiments, a zone may be given a name that is different than the device(s) belonging to the zone. For example, Zone B in FIG. 3A is named "Stereo" but none of the devices in Zone B have this name. In one aspect, Zone B is a single UI entity representing a single device named "Stereo," composed of constituent devices "Bed 1" and "Bed 2." In one implementation, the Bed 1 device may be playback device 102*f* in the master bedroom 101*b* (FIG. 1A) and the Bed 2 device may be the playback device 102*g* also in the master bedroom 101*b* (FIG. 1A).

As noted above, playback devices that are bonded may have different playback responsibilities, such as playback responsibilities for certain audio channels. For example, as shown in FIG. 3B, the Bed 1 and Bed 2 devices 102*f* and 102*g* may be bonded so as to produce or enhance a stereo effect of audio content. In this example, the Bed 1 playback device 102*f* may be configured to play a left channel audio component, while the Bed 2 playback device 102*g* may be configured to play a right channel audio component. In some implementations, such stereo bonding may be referred to as "pairing."

Additionally, playback devices that are configured to be bonded may have additional and/or different respective speaker drivers. As shown in FIG. 3C, the playback device 102*b* named "Front" may be bonded with the playback device 102*k* named "SUB." The Front device 102*b* may render a range of mid to high frequencies, and the SUB device 102*k* may render low frequencies as, for example, a subwoofer. When unbonded, the Front device 102*b* may be configured to render a full range of frequencies. As another example, FIG. 3D shows the Front and SUB devices 102*b* and 102*k* further bonded with Right and Left playback devices 102*a* and 102*j*, respectively. In some implementations, the Right and Left devices 102*a* and 102*j* may form surround or "satellite" channels of a home theater system. The bonded playback devices 102*a*, 102*b*, 102*j*, and 102*k* may form a single Zone D (FIG. 3A).

In some implementations, playback devices may also be "merged." In contrast to certain bonded playback devices, playback devices that are merged may not have assigned playback responsibilities, but may each render the full range of audio content that each respective playback device is capable of. Nevertheless, merged devices may be represented as a single UI entity (i.e., a zone, as discussed above). For instance, FIG. 3E shows the playback devices 102*d* and 102*m* in the Living Room merged, which would result in these devices being represented by the single UI entity of Zone C. In one embodiment, the playback devices 102*d* and

102*m* may playback audio in synchrony, during which each outputs the full range of audio content that each respective playback device 102*d* and 102*m* is capable of rendering.

In some embodiments, a stand-alone NMD may be in a zone by itself. For example, the NMD 103*h* from FIG. 1A is named "Closet" and forms Zone I in FIG. 3A. An NMD may also be bonded or merged with another device so as to form a zone. For example, the NMD device 103*f* named "Island" may be bonded with the playback device 102*i* Kitchen, which together form Zone F, which is also named "Kitchen." Additional details regarding assigning NMDs and playback devices as designated or default devices may be found, for example, in previously referenced U.S. patent application Ser. No. 15/438,749. In some embodiments, a stand-alone NMD may not be assigned to a zone.

Zones of individual, bonded, and/or merged devices may be arranged to form a set of playback devices that playback audio in synchrony. Such a set of playback devices may be referred to as a "group," "zone group," "synchrony group," or "playback group." In response to inputs provided via a controller device 104, playback devices may be dynamically grouped and ungrouped to form new or different groups that synchronously play back audio content. For example, referring to FIG. 3A, Zone A may be grouped with Zone B to form a zone group that includes the playback devices of the two zones. As another example, Zone A may be grouped with one or more other Zones C-I. The Zones A-I may be grouped and ungrouped in numerous ways. For example, three, four, five, or more (e.g., all) of the Zones A-I may be grouped. When grouped, the zones of individual and/or bonded playback devices may play back audio in synchrony with one another, as described in previously referenced U.S. Pat. No. 8,234,395. Grouped and bonded devices are example types of associations between portable and stationary playback devices that may be caused in response to a trigger event, as discussed above and described in greater detail below.

In various implementations, the zones in an environment may be assigned a particular name, which may be the default name of a zone within a zone group or a combination of the names of the zones within a zone group, such as "Dining Room+Kitchen," as shown in FIG. 3A. In some embodiments, a zone group may be given a unique name selected by a user, such as "Nick's Room," as also shown in FIG. 3A. The name "Nick's Room" may be a name chosen by a user over a prior name for the zone group, such as the room name "Master Bedroom."

Referring back to FIG. 2A, certain data may be stored in the memory 213 as one or more state variables that are periodically updated and used to describe the state of a playback zone, the playback device(s), and/or a zone group associated therewith. The memory 213 may also include the data associated with the state of the other devices of the MPS 100, which may be shared from time to time among the devices so that one or more of the devices have the most recent data associated with the system.

In some embodiments, the memory 213 of the playback device 102 may store instances of various variable types associated with the states. Variables instances may be stored with identifiers (e.g., tags) corresponding to type. For example, certain identifiers may be a first type "a1" to identify playback device(s) of a zone, a second type "b1" to identify playback device(s) that may be bonded in the zone, and a third type "c1" to identify a zone group to which the zone may belong. As a related example, in FIG. 1A, identifiers associated with the Patio may indicate that the Patio is the only playback device of a particular zone and not in a zone group. Identifiers associated with the Den may indicate that the Den is not grouped with other zones but includes bonded playback devices 102*a*, 102*b*, 102*j*, and 102*k*. Identifiers associated with the Dining Room may indicate that the Dining Room is part of Dining Room+ Kitchen group and that devices 103*f* and 102*i* are bonded. Identifiers associated with the Kitchen may indicate the same or similar information by virtue of the Kitchen being part of the Dining Room+Kitchen zone group. Other example zone variables and identifiers are described below.

In yet another example, the MPS 100 may include variables or identifiers representing other associations of zones and zone groups, such as identifiers associated with Areas, as shown in FIG. 3A. An Area may involve a cluster of zone groups and/or zones not within a zone group. For instance, FIG. 3A shows a first area named "First Area" and a second area named "Second Area." The First Area includes zones and zone groups of the Patio, Den, Dining Room, Kitchen, and Bathroom. The Second Area includes zones and zone groups of the Bathroom, Nick's Room, Bedroom, and Living Room. In one aspect, an Area may be used to invoke a cluster of zone groups and/or zones that share one or more zones and/or zone groups of another cluster. In this respect, such an Area differs from a zone group, which does not share a zone with another zone group. Further examples of techniques for implementing Areas may be found, for example, in U.S. application Ser. No. 15/682,506 filed Aug. 21, 2017 and titled "Room Association Based on Name," and U.S. Pat. No. 8,483,853 filed Sep. 11, 2007, and titled "Controlling and manipulating groupings in a multi-zone media system." Each of these applications is incorporated herein by reference in its entirety.

The memory 213 may be further configured to store other data. Such data may pertain to audio sources accessible by the playback device 102 or a playback queue that the playback device (or some other playback device(s)) may be associated with. In embodiments described below, the memory 213 is configured to store a set of command data for selecting a particular VAS when processing voice inputs. During operation, one or more playback zones in the environment of FIG. 1A may each be playing different audio content. For instance, the user may be grilling in the Patio zone and listening to hip hop music being played by the playback device 102*c*, while another user may be preparing food in the Kitchen zone and listening to classical music being played by the playback device 102*i*. In another example, a playback zone may play the same audio content in synchrony with another playback zone.

For instance, the user may be in the Office zone where the playback device 102*n* is playing the same hip-hop music that is being playing by playback device 102*c* in the Patio zone. In such a case, playback devices 102*c* and 102*n* may be playing the hip-hop in synchrony such that the user may seamlessly (or at least substantially seamlessly) enjoy the audio content that is being played out-loud while moving between different playback zones. Synchronization among playback zones may be achieved in a manner similar to that of synchronization among playback devices, as described in previously referenced U.S. Pat. No. 8,234,395.

As suggested above, the zone configurations of the MPS 100 may be dynamically modified. As such, the MPS 100 may support numerous configurations. For example, if a user physically moves one or more playback devices to or from a zone, the MPS 100 may be reconfigured to accommodate the change(s). For instance, if the user physically moves the playback device 102*c* from the Patio zone to the Office zone, the Office zone may now include both the playback devices 102*c* and 102*n*. In some cases, the user may pair or group the moved playback device 102*c* with the Office zone and/or rename the players in the Office zone using, for example, one of the controller devices 104 and/or voice input. As another example, if one or more playback devices 102 are moved to a particular space in the home environment that is not already a playback zone, the moved playback device(s) may be renamed or associated with a playback zone for the particular space.

Further, different playback zones of the MPS 100 may be dynamically combined into zone groups or split up into individual playback zones. For example, the Dining Room zone and the Kitchen zone may be combined into a zone group for a dinner party such that playback devices 102*i* and 102*l* may render audio content in synchrony. As another example, bonded playback devices in the Den zone may be split into (i) a television zone and (ii) a separate listening zone. The television zone may include the Front playback device 102*b*. The listening zone may include the Right, Left, and SUB playback devices 102*a*, 102*j*, and 102*k*, which may be grouped, paired, or merged, as described above. Splitting the Den zone in such a manner may allow one user to listen to music in the listening zone in one area of the living room space, and another user to watch the television in another area of the living room space. In a related example, a user may utilize either of the NMD 103*a* or 103*b* (FIG. 1B) to control the Den zone before it is separated into the television zone and the listening zone. Once separated, the listening zone may be controlled, for example, by a user in the vicinity of the NMD 103*a*, and the television zone may be controlled, for example, by a user in the vicinity of the NMD 103*b*. As described above, however, any of the NMDs 103 may be configured to control the various playback and other devices of the MPS 100.

c. Example Controller Devices

FIG. 4 is a functional block diagram illustrating certain aspects of a selected one of the controller devices 104 of the MPS 100 of FIG. 1A. Such controller devices may also be referred to herein as a "control device" or "controller." The controller device shown in FIG. 4 may include components that are generally similar to certain components of the network devices described above, such as a processor 412, memory 413 storing program software 414, at least one network interface 424, and one or more microphones 422. In one example, a controller device may be a dedicated controller for the MPS 100. In another example, a controller device may be a network device on which media playback system controller application software may be installed, such as for example, an iPhone™, iPad™ or any other smart phone, tablet, or network device (e.g., a networked computer such as a PC or Mac™).

The memory 413 of the controller device 104 may be configured to store controller application software and other data associated with the MPS 100 and/or a user of the system 100. The memory 413 may be loaded with instructions in software 414 that are executable by the processor 412 to achieve certain functions, such as facilitating user access, control, and/or configuration of the MPS 100. The controller device 104 is configured to communicate with other network devices via the network interface 424, which may take the form of a wireless interface, as described above.

In one example, system information (e.g., such as a state variable) may be communicated between the controller device 104 and other devices via the network interface 424. For instance, the controller device 104 may receive playback zone and zone group configurations in the MPS 100 from a playback device, an NMD, or another network device. Likewise, the controller device 104 may transmit such system information to a playback device or another network device via the network interface 424. In some cases, the other network device may be another controller device.

The controller device 104 may also communicate playback device control commands, such as volume control and audio playback control, to a playback device via the network interface 424. As suggested above, changes to configurations of the MPS 100 may also be performed by a user using the controller device 104. The configuration changes may include adding/removing one or more playback devices to/from a zone, adding/removing one or more zones to/from a zone group, forming a bonded or merged player, separating one or more playback devices from a bonded or merged player, among others.

As shown in FIG. 4, the controller device 104 also includes a user interface 440 that is generally configured to facilitate user access and control of the MPS 100. The user interface 440 may include a touch-screen display or other physical interface configured to provide various graphical controller interfaces, such as the controller interfaces 540a and 540b shown in FIGS. 5A and 5B. Referring to FIGS. 5A and 5B together, the controller interfaces 540a and 540b includes a playback control region 542, a playback zone region 543, a playback status region 544, a playback queue region 546, and a sources region 548. The user interface as shown is just one example of an interface that may be provided on a network device, such as the controller device shown in FIG. 4, and accessed by users to control a media playback system, such as the MPS 100. Other user interfaces of varying formats, styles, and interactive sequences may alternatively be implemented on one or more network devices to provide comparable control access to a media playback system.

The playback control region 542 (FIG. 5A) may include selectable icons (e.g., by way of touch or by using a cursor) that, when selected, cause playback devices in a selected playback zone or zone group to play or pause, fast forward, rewind, skip to next, skip to previous, enter/exit shuffle mode, enter/exit repeat mode, enter/exit cross fade mode, etc. The playback control region 542 may also include selectable icons that, when selected, modify equalization settings and/or playback volume, among other possibilities.

The playback zone region 543 (FIG. 5B) may include representations of playback zones within the MPS 100. The playback zones regions 543 may also include a representation of zone groups, such as the Dining Room+Kitchen zone group, as shown.

In some embodiments, the graphical representations of playback zones may be selectable to bring up additional selectable icons to manage or configure the playback zones in the MPS 100, such as a creation of bonded zones, creation of zone groups, separation of zone groups, and renaming of zone groups, among other possibilities.

For example, as shown, a "group" icon may be provided within each of the graphical representations of playback zones. The "group" icon provided within a graphical representation of a particular zone may be selectable to bring up options to select one or more other zones in the MPS 100 to be grouped with the particular zone. Once grouped, playback devices in the zones that have been grouped with the particular zone will be configured to play audio content in synchrony with the playback device(s) in the particular zone. Analogously, a "group" icon may be provided within a graphical representation of a zone group. In this case, the "group" icon may be selectable to bring up options to deselect one or more zones in the zone group to be removed from the zone group. Other interactions and implementations for grouping and ungrouping zones via a user interface are also possible. The representations of playback zones in the playback zone region 543 (FIG. 5B) may be dynamically updated as playback zone or zone group configurations are modified.

The playback status region 544 (FIG. 5A) may include graphical representations of audio content that is presently being played, previously played, or scheduled to play next in the selected playback zone or zone group. The selected playback zone or zone group may be visually distinguished on a controller interface, such as within the playback zone region 543 and/or the playback status region 544. The graphical representations may include track title, artist name, album name, album year, track length, and/or other relevant information that may be useful for the user to know when controlling the MPS 100 via a controller interface.

The playback queue region 546 may include graphical representations of audio content in a playback queue associated with the selected playback zone or zone group. In some embodiments, each playback zone or zone group may be associated with a playback queue comprising information corresponding to zero or more audio items for playback by the playback zone or zone group. For instance, each audio item in the playback queue may comprise a uniform resource identifier (URI), a uniform resource locator (URL), or some other identifier that may be used by a playback device in the playback zone or zone group to find and/or retrieve the audio item from a local audio content source or a networked audio content source, which may then be played back by the playback device.

In one example, a playlist may be added to a playback queue, in which case information corresponding to each audio item in the playlist may be added to the playback queue. In another example, audio items in a playback queue may be saved as a playlist. In a further example, a playback queue may be empty, or populated but "not in use" when the playback zone or zone group is playing continuously streamed audio content, such as Internet radio that may continue to play until otherwise stopped, rather than discrete audio items that have playback durations. In an alternative embodiment, a playback queue can include Internet radio and/or other streaming audio content items and be "in use" when the playback zone or zone group is playing those items. Other examples are also possible.

When playback zones or zone groups are "grouped" or "ungrouped," playback queues associated with the affected playback zones or zone groups may be cleared or re-associated. For example, if a first playback zone including a first playback queue is grouped with a second playback zone including a second playback queue, the established zone group may have an associated playback queue that is initially empty, that contains audio items from the first playback queue (such as if the second playback zone was added to the first playback zone), that contains audio items from the second playback queue (such as if the first playback zone was added to the second playback zone), or a combination of audio items from both the first and second playback queues. Subsequently, if the established zone group is ungrouped, the resulting first playback zone may be re-associated with the previous first playback queue or may be associated with a new playback queue that is empty or contains audio items from the playback queue associated with the established zone group before the established zone group was ungrouped. Similarly, the resulting second playback zone may be re-associated with the previous second playback queue or may be associated with a new playback queue that is empty or contains audio items from the playback queue associated with the established zone group before the established zone group was ungrouped. Other examples are also possible.

With reference still to FIGS. 5A and 5B, the graphical representations of audio content in the playback queue region 646 (FIG. 5A) may include track titles, artist names, track lengths, and/or other relevant information associated with the audio content in the playback queue. In one example, graphical representations of audio content may be selectable to bring up additional selectable icons to manage and/or manipulate the playback queue and/or audio content represented in the playback queue. For instance, a represented audio content may be removed from the playback queue, moved to a different position within the playback queue, or selected to be played immediately, or after any currently playing audio content, among other possibilities. A playback queue associated with a playback zone or zone group may be stored in a memory on one or more playback devices in the playback zone or zone group, on a playback device that is not in the playback zone or zone group, and/or some other designated device. Playback of such a playback queue may involve one or more playback devices playing back media items of the queue, perhaps in sequential or random order.

The sources region 548 may include graphical representations of selectable audio content sources and/or selectable voice assistants associated with a corresponding VAS. The VASes may be selectively assigned. In some examples, multiple VASes, such as AMAZON's Alexa, MICROSOFT's Cortana, etc., may be invokable by the same NMD. In some embodiments, a user may assign a VAS exclusively to one or more NMDs. For example, a user may assign a first VAS to one or both of the NMDs 103a and 103b in the Den shown in FIG. 1A, and a second VAS to the NMD 103f in the Kitchen. Other examples are possible.

d. Example Audio Content Sources

The audio sources in the sources region 548 may be audio content sources from which audio content may be retrieved and played by the selected playback zone or zone group. One or more playback devices in a zone or zone group may be configured to retrieve for playback audio content (e.g., according to a corresponding URI or URL for the audio content) from a variety of available audio content sources. In one example, audio content may be retrieved by a playback device directly from a corresponding audio content source (e.g., via a line-in connection). In another example, audio content may be provided to a playback device over a network via one or more other playback devices or network devices. As described in greater detail below, in some embodiments audio content may be provided by one or more media content services.

Example audio content sources may include a memory of one or more playback devices in a media playback system such as the MPS 100 of FIG. 1, local music libraries on one or more network devices (e.g., a controller device, a network-enabled personal computer, or a networked-attached storage ("NAS")), streaming audio services providing audio content via the Internet (e.g., cloud-based music services), or audio sources connected to the media playback system via a line-in input connection on a playback device or network device, among other possibilities.

In some embodiments, audio content sources may be added or removed from a media playback system such as the MPS 100 of FIG. 1A. In one example, an indexing of audio items may be performed whenever one or more audio content sources are added, removed, or updated. Indexing of audio items may involve scanning for identifiable audio items in all folders/directories shared over a network accessible by playback devices in the media playback system and generating or updating an audio content database comprising metadata (e.g., title, artist, album, track length, among others) and other associated information, such as a URI or URL for each identifiable audio item found. Other examples for managing and maintaining audio content sources may also be possible.

Figure 6:
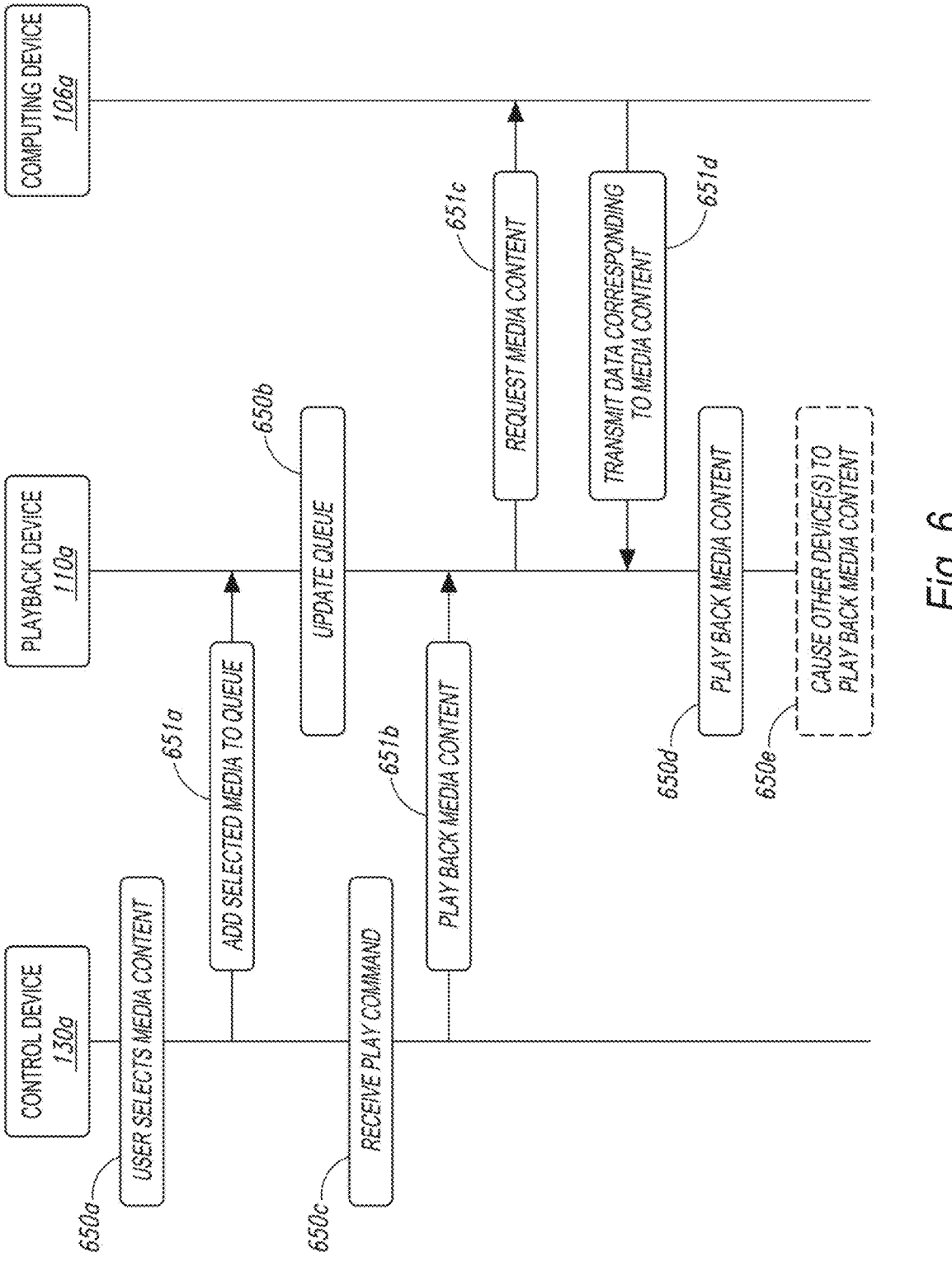
FIG. 6 is a message flow diagram of a media playback system.

FIG. 6 is a message flow diagram illustrating data exchanges between devices of the MPS 100. At step 650a, the MPS 100 receives an indication of selected media content (e.g., one or more songs, albums, playlists, podcasts, videos, stations) via the control device 104. The selected media content can comprise, for example, media items stored locally on one or more devices (e.g., the audio source 105 of FIG. 1C) connected to the media playback system and/or media items stored on one or more media service servers (one or more of the remote computing devices 106 of FIG. 1B). In response to receiving the indication of the selected media content, the control device 104 transmits a message 651a to the playback device 102 (FIGS. 1A-1C) to add the selected media content to a playback queue on the playback device 102.

At step 650b, the playback device 102 receives the message 651a and adds the selected media content to the playback queue for play back.

At step 650c, the control device 104 receives input corresponding to a command to play back the selected media content. In response to receiving the input corresponding to the command to play back the selected media content, the control device 104 transmits a message 651b to the playback device 102 causing the playback device 102 to play back the selected media content. In response to receiving the message 651b, the playback device 102 transmits a message 651c to the computing device 106 requesting the selected media content. The computing device 106, in response to receiving the message 651c, transmits a message 651d comprising data (e.g., audio data, video data, a URL, a URI) corresponding to the requested media content.

At step 650d, the playback device 102 receives the message 651d with the data corresponding to the requested media content and plays back the associated media content.

At step 650e, the playback device 102 optionally causes one or more other devices to play back the selected media content. In one example, the playback device 102 is one of a bonded zone of two or more players (FIG. 1M). The playback device 102 can receive the selected media content and transmit all or a portion of the media content to other devices in the bonded zone. In another example, the playback device 102 is a coordinator of a group and is configured to transmit and receive timing information from one or more other devices in the group. The other one or more devices in the group can receive the selected media content from the computing device 106, and begin playback of the selected media content in response to a message from the playback device 102 such that all of the devices in the group play back the selected media content in synchrony.

Within examples, such messages may conform to one or more protocols or interfaces (e.g., an Application Programming Interface). A platform API may support one or more namespaces that include controllable resources (e.g., the playback devices 102 and features thereof). Various functions may modify the resources and thereby control actions on the playback devices 102. For instance, HTTP request methods such as GET and POST may request and modify various resources in a namespace. Example namespaces in a platform API include playback (including controllable resources for playback), playbackMetadata (including metadata resources related to playback), volume (including resources for volume control), playlist (including resources for queue management), and groupVolume (including resources for volume control of a synchrony group), among other examples. Among other examples, such messages may conform to a standard, such as universal-plug-and-play (uPnP).

III. Example Scent Diffusing System

Example systems and techniques described herein relate to a scent diffusing system. The scent diffusing system may include one or more individual scent diffusing devices which may be given names during the setup process. The scent diffusing system can hold more than one canister containing scented oil and be programmable to combine or mix oils from different canisters to produce a fragrance that is diffused into an area (e.g., room, zone).

Figure 7:
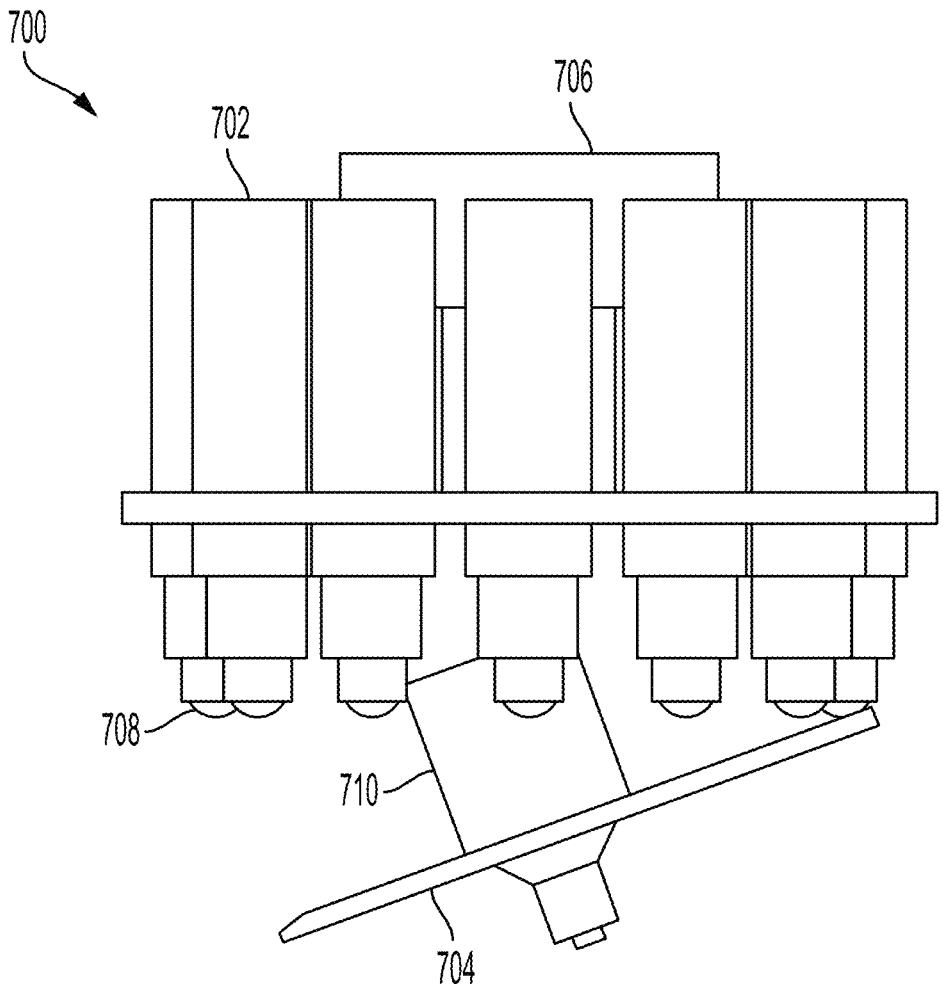
FIG. 7 illustrates an example scent diffusing system.

FIG. 7 illustrates an example scent diffusing device or system 700. The scent diffusing system 700 can include one or more canisters 702 containing oils with different scents arranged in a manner that allows oils to be dispersed from different canisters 702 onto a common surface, a dispensing system 704 that can be configured to discharge a programmable amount of oil from each canister, and a fan 706 to disperse the scent of the oils in an area. In this example, the opening of each canister may be directed downward and sealed with a ball 708 having a diameter larger than the diameter of the canister opening such that when force is not applied to the ball 708 the canister is sealed. The dispensing system 704 may apply an upward force on the ball 708 to open the canister and release oil. The amount of oil released can be controlled through the amount of force applied to the ball 708 and/or the duration of the applied force. The fan 706 may cause the scent of the released oil to be dispersed in an area. The scent diffusing system 700 includes a motor 710 to rotate the dispensing system and release oil from different canisters 702. The diffusing system may contain a heating element (e.g., heated plate) (not shown) to heat the released oil and release the fragrance into the environment. The radius of diffusion can be controlled by controlling the speed of the fan. For a localized fragrance, the fan may be turned off or a low speed may be used. For a fragrance with wider dispersion, a high fan speed may be used and/or the release of the fragrance may be coordinated with a fan in, for example, a HVAC system.

Figure 8:
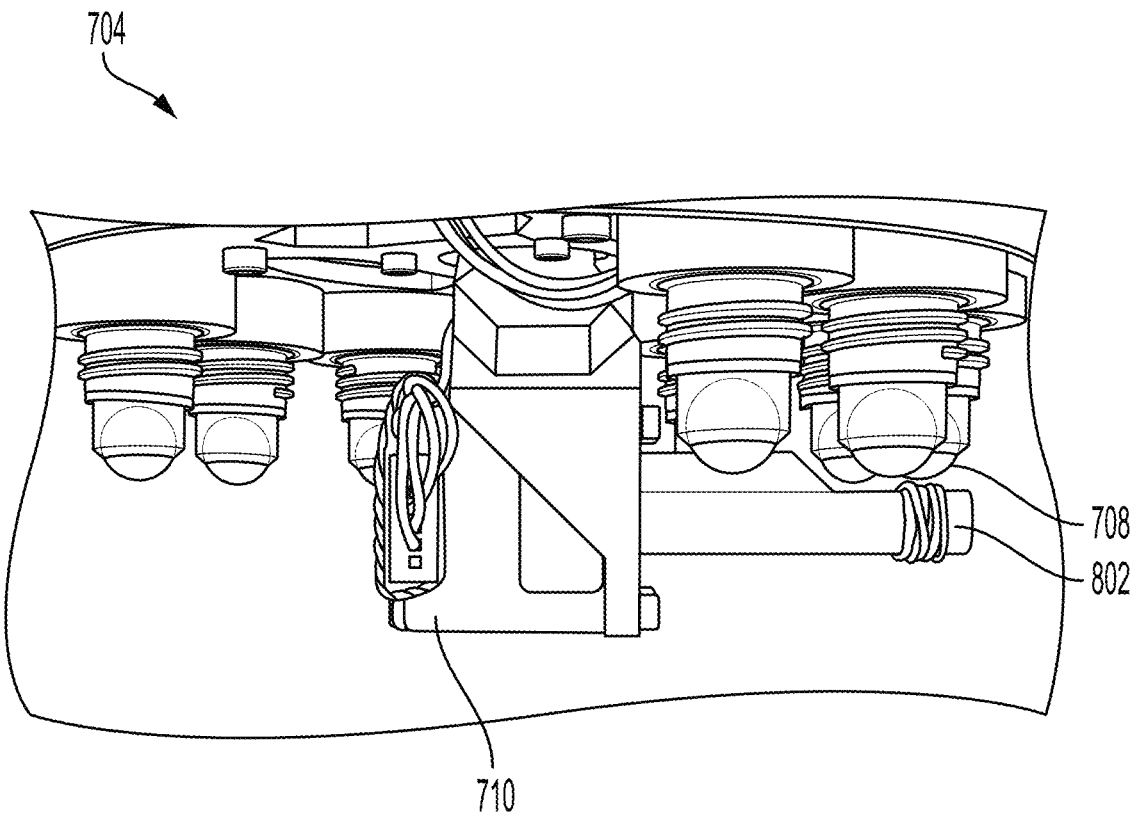
FIG. 8 shows is a side view of the example dispensing system.
Figure 9:
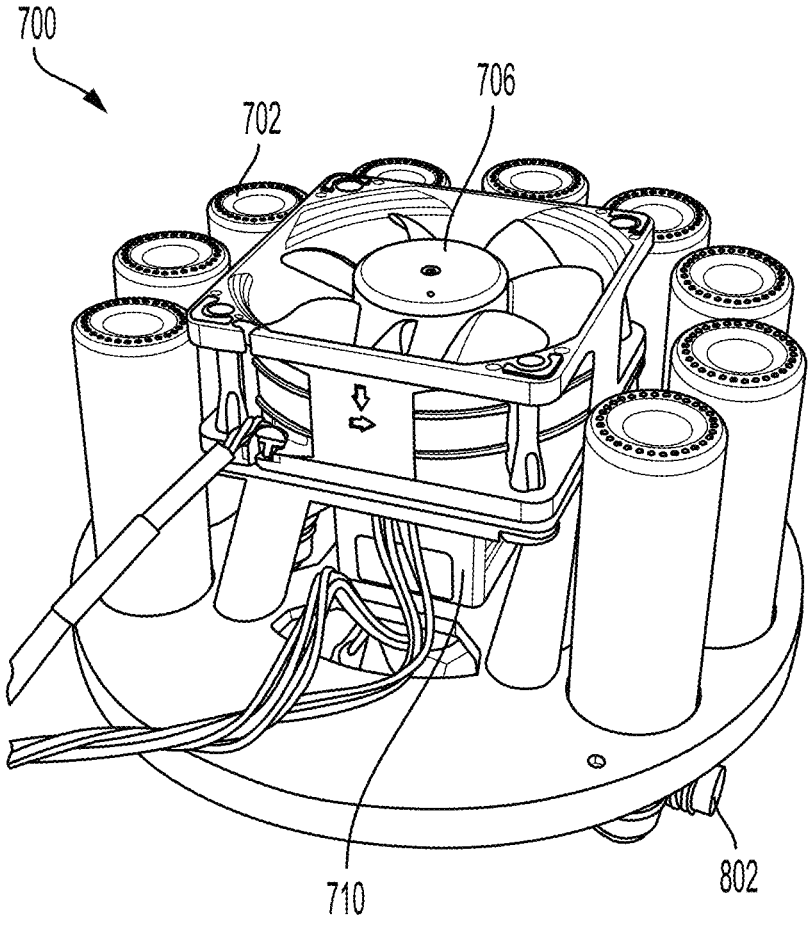
FIG. 9 shows a top view of the example dispensing system.

FIG. 8 shows a side view of the example dispensing system 704 and FIG. 9 is a top view of the scent diffusing system 700. The dispensing system may include an arm 802 and the motor 710 to rotate the arm 802 under different canisters 702. When the arm 802 is tilted upwards, the arm 802 makes contact with the ball 708 and releases oils. The arm can have a receptacle for the oil. The dispensing system 704 can be programmed to receive various amounts of oils to produce a desired fragrance. The fragrance is formed by component scented oils combined from the different canisters 702.

Other examples of the scent diffusing system 700 are possible. In another example, the programmable release mechanism may be included in each canister and each canister may include an electronically controllable nozzle. The arm may rotate under a particular canister 702 and the dispenser controller may send a command to the canister 702 to open the nozzle for a predetermined duration of time based on the flow rate of oil out of the nozzle. After the end of the duration of time, the dispenser controller may they send a command to the motor 710 to rotate the arm under the second canister and similarly command the second canister 702 to open the nozzle for a duration of time. In some aspects, the oil may be discharged from the canister by applying force to the body of non-rigid (e.g., rubber, plastic, silicone) canister. For example, the amount of oil may be measured as a number of drops which are extruded from the canister when the body is squeezed.

The arm may contain a heating element to heat the oil. In other examples, the arm may be at an upwards angle such that all oil received from the different canisters flows into the center of the dispensing system under the fan. The center of the dispensing system can contain the heating element.

In some examples, the scent diffusing system may be combined with a playback device to provide both audio playback and fragrance in a room, such as any of the playback devices 102 discussed above and shown in FIGS. 1A-2B. The scent diffusing system may be disposed within the housing of or integrated into the playback device 102.

The scent diffusing system may include a network interface that can communicate with other devices over a wired or wireless connection to receive and/or send commands and other data. The communication with other devices (e.g., playback devices 102, network microphone devices 103, illumination device 108, smart thermostat 110, local computing device 105) may be over the networks 107 and/or the local area network 111. The scent diffusing system can be controlled using a control interface on the system (e.g., control area 232) and/or a controller device such as controller device 104. The controller device can be used to select the component oils to use and amounts of each component oil to use in the mix. The amounts can be measured using, for example, weight, release time, relative ratios (e.g., percentage, 2:1), applied force based on total amount of oil for the fragrance or the desired strength of the fragrance. The oil can be in fluid form which is then heated after discharge to evaporate the oil and release the scent of the oil.

The scent diffusing system may include a canister recognition system that identifies the scented oil contained within the canister when the canister is inserted into the scent diffusing system. For example, the identification system may be a scanner that can recognize a code (e.g., serial number, barcode, QR code) on the external surface of the canister. In another example, the identification system may be a wireless identification system that uses radio-frequency identification (RFID), near-field communication (NFC), or Bluetooth technologies, among other possibilities. The scent diffusing system can determine when a canister is low in oil based on a visual scan of the oil level in the canister made of a transparent or semi-transparent material (e.g., glass, plastic) and/or weight of the canister. The low oil threshold may be a default set by the system or set by the user, for example, as a percentage of a full container (e.g., 0%, 10%, 15%). When the scent diffusing system determines that a canister has reached a low oil level threshold, the scent diffusing system can submit an order for a refill of the canister. This feature may be provided to subscribers of a refill service. A user may create an account during the setup process for the scent diffusing device and use the account to manage subscriptions.

In another aspect of the scent diffusing system, the scent diffusing system can automatically diffuse scents. For example, the scent diffusing system can be associated with or included in a scene, routine, or quickstart such that a particular fragrance is released when a scene, routine, or quickstart is activated. Additional details regarding scenes, routines, or quickstarts may be found in U.S. Pat. No. 8,483,853 filed on Sep. 11, 2007 and titled "CONTROLLING AND MANIPULATING GROUPINGS IN A MULTIZONE MEDIA SYSTEM, U.S. Patent Application Publication No. 2020/0183640 filed on Jun. 9, 2019 and titled "SELECTION OF PLAYBACK DEVICES," and U.S. patent application Ser. No. 17/953,896 filed on Sep. 27, 2022 and titled "ROUTINES FOR PLAYBACK DEVICES," which are all hereby incorporated by reference in their entirety.

In one example, a first scene, quickstart, or routine may be associated with an activity such as getting ready for sleep such that activation of the sleep scene, quickstart, or routine causes diffusion of a "sleep" fragrance and playback of a "sleep" playlist. Different fragrances may be automatically released at different times in the day and in specific rooms within the home through the use of scenes or routines. The quickstart or routine may specify a name of the fragrance to use which can correspond to a particular mix of oil and the fan speed for fast or slow and/or silent diffusion of the fragrance.

As yet another example, a scene that is activated as a morning alarm may be a "wake-up" scene. The alarm for the "wake-up" scene may be set to be activated at 6:00 am to play back audio content in the bedroom, turn on one or more smart illumination devices 108 in the bedroom, and release the "morning" fragrance in the bedroom.

As another example, a "wake-up" schedule may be a set of routines that activate certain events as a sequence of actions or routines. The release of the fragrance can be performed before the alarm to allow for wider dispersion of the fragrance prior to the user waking up to the morning alarm. The fragrance could be set to initiate release at a relative time (e.g., 15 minutes) prior to or at a predetermined time (e.g., 5:45 am) before the alarm is played. In some instances, the devices associated with "wake-up" scene may be same or different from the devices associated with the "sleep" scene. As an example, devices associated with the "sleep" scene might be playback devices and/or scent diffusing devices in the bedroom while devices associated with the "wake-up" scene might include devices in the bathroom or kitchen in addition to or instead of the devices associated with the "sleep" scene.

In some examples, the fragrance can be a predetermined mix of oil from one or more canisters in the scent diffusing system. The mix of the oil can be user defined and/or may be based on recipes provided via the networks 107 that were submitted by other users. The selected recipes can be based on the type of music being played (e.g., playlist, radio station, genre, beats per minute, etc.), the setting (e.g., home, work, café, retail), number of people in the room, who is in the room, environment (e.g., weather, room name, etc.) and/or the type of content being consumed (e.g., TV, movie, gaming, etc.). The available recipes may be filtered to those that match canister oils that are installed in the user's scent diffusing system. For example, a recipe for a scent may call for oil A, oil B, and oil C, and the user may have only oil A, oil C, and oil D, and thus, this scent might not be made available for selection. The scent diffusing system may check oil levels in the canister to confirm that there is oil remaining before surfacing recipes requiring that particular oil. In some instances, recipes may be matched or selected based on similar names, keywords, and/or tags. For example, a recipe associated with "calm" or "relaxing" may be surfaced or selected for a "sleep" or "relax" scene.

In another aspect of the scent diffusing system, multiple individual scent diffusing systems may be placed in a single room. A user may group the scent diffusing system into a saved group. For example, a living room may have two scent diffusing systems, and both scent diffusing systems can be automatically selected when the "living room" scent diffusing system is selected. The individual scent diffusing systems may release the same or different scents within the room and a single control can control the diffusion strength of the scents in the room. For example, the first scent diffusing system may be set to diffuse its scent at half the strength of the second diffusing system in the room. When the fragrance strength for the living room is adjusted, the relative ratio between the first scent diffusing system and the second scent diffusing system is maintained.

Over time, the remaining oil on the hot plate can be reduced through the oil being burned off and/or being dried out. After a period of time, the components for the scent may be refilled or replenished by repeating collection of component oils according to the recipe. The period of time may be determined based on the amount of total oil in the mixture. In some aspects, the heat of the hot plate may be cycled on and off, for example, being turned on for 5 minutes and turned off for 10 minutes.

In another example, the fragrance strength may be gradually increased or changed over time. Because the nose becomes desensitized to aromas over time, the strength of the fragrance may need to be increased at a specific rate and/or incrementally increased at the end of a duration of time and/or the fragrance mix of the component oils forming the fragrance may be changed. The recipe may be adjusted removing and/or substituting components or changing the ratios of the component oils in the recipe.

The scent diffusing system can include a directional component. The fragrance for an area or room may be composed of multiple scent mixes or recipes, and each recipe may be diffused in a particular direction and/or a particular location in the room. For example, for an outdoor ambience or scene, a recipe for cedar tree scent may be used in the center of the room, a pine tree recipe is dispersed on the right side of the room, and an oak tree scent is diffused on the left side of the room. The different recipes may be dispersed from a scent diffusing system containing three dispensing systems and/or three scent diffusing systems in the same room.

In some aspects of the scent diffusing system, the scent diffusing system may communicate over network 107 to coordinate diffusion of fragrances with other households. For example, a first household may be mirroring playback with a second household such that the first and second households are listening to the same content. Similar to mirroring content playback, scents can be mirrored across households such that the same scent is diffused in the space in response to playback of the same content and/or the scent diffusing systems can be coordinated to release the same fragrance at the same point in time (e.g., 5 pm, 1 hour into playback). Further details on mirroring content playback can be found in U.S. Pat. No. 10,587,693 filed on Apr. 1, 2014 and titled "Mirrored queues," which is hereby incorporated by reference in its entirety.

Figure 10:
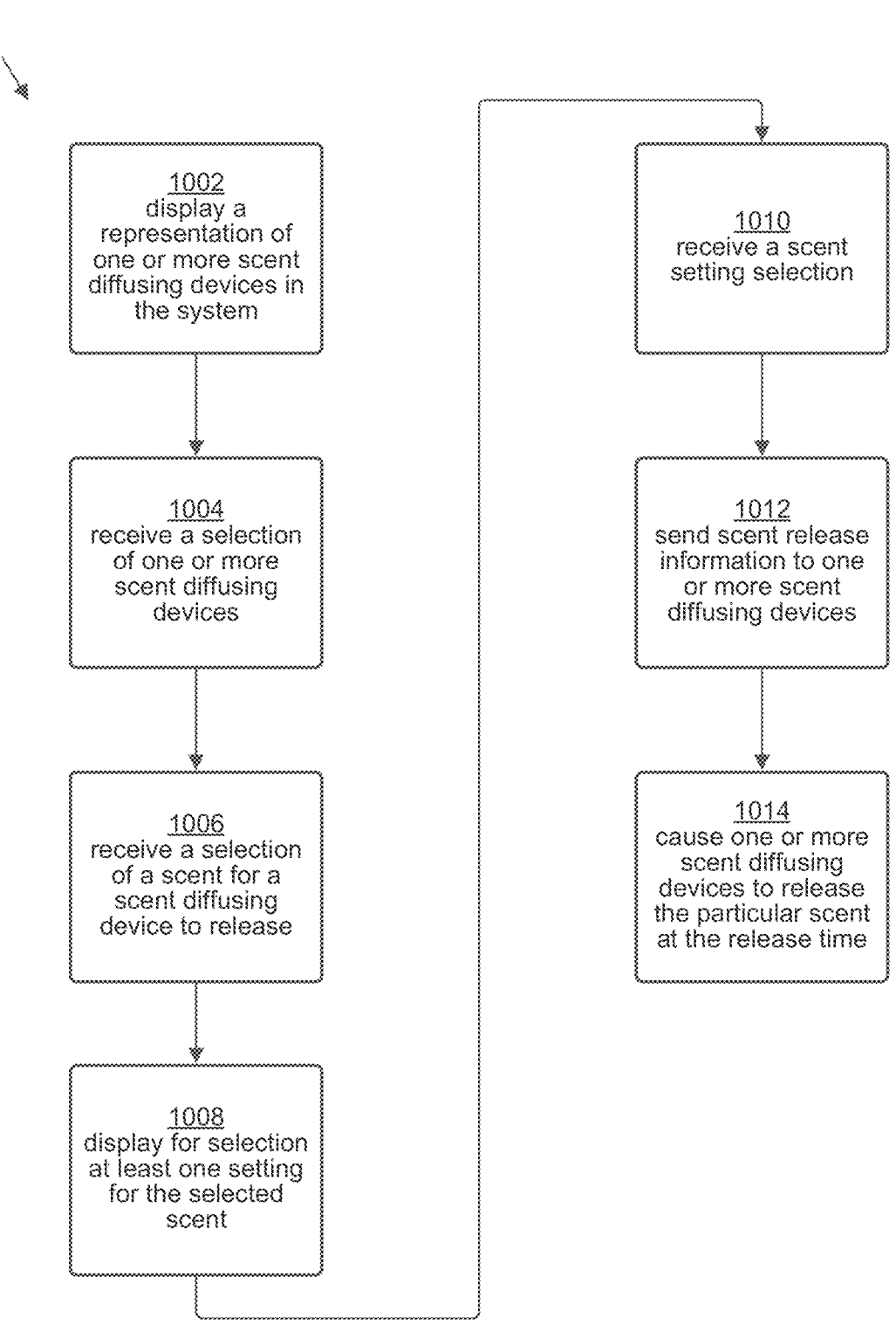
FIG. 10 shows a flow diagram of an example method for selecting scents and scent diffusing devices.

FIG. 10 shows a flow diagram of an example method 1000 for selecting scents and scent diffusing devices in the system to release the selected scent. At block 1002, a controller device may display a representation of one or more scent diffusing devices in the system for selection by the user. The controller device may perform a discovery on the network to identify available scent diffusing devices in the home, and display the available scent diffusing devices to the user.

At block 1004, the user can select from the displayed scent diffusing devices. For example, a "bedroom" scent diffusing device and a "kitchen" scent diffusing device may be available for scent diffusion. At block 1006, the user may select a scent for diffusion. The system may store in one or more devices, or may obtain from a remote server, recipes available to the system based on the canisters installed in the available scent diffusing devices. The available recipes may be displayed to the user for selection. As an example, the controller device may have received a selection of the "bedroom" scent diffusing device at block 1004, and the controller device may have received a selection of the "nap" scent in block 1006. At block 1008, the controller device may display to the user settings for the scent diffusion. The settings can include duration of scent release (e.g., 1 hour), a scent strength setting (e.g., in a range from 0-10), or media content for playback (e.g., an album, playlist, radio station etc.). At block 1010, the user may select a "sleep" playlist for playback for the duration of the scent release by the "bedroom" scent diffusion device and/or other playback devices grouped with the "bedroom" scent diffusion device. The user may elect to release the scent immediately or to delay the release.

At block 1012, the controller device may transmit this information in one or more messages to the selected scent diffusion device including the selected scent, selected scent diffusing devices, duration, strength, and/or media content for playback.

At block 1014, the scent diffusion system may cause the release of the scent at the desired time based on the information received from the controller device.

FIG. 11 shows an example method 1100 of creating a scent scene. At block 1102, the user may select the option to create a scent scene. At block 1104, the system may identify available scent diffusing devices in the system and obtain recipe information for scents that are available for diffusion by scent diffusing devices in the system as described herein. At block 1106, the available scents and scent diffusing devices may be provided to the user for selection of scents and one or more diffusing devices to diffuse the selected scent. At block 1108, the system may receive the selection of the scent and scent diffusing device(s). At block 1110, the system may store the scent scene with a name to identify the scene. The scene can include information about the selected scent and scent diffusing devices to use for the scent when the scene is activated. This information may be disseminated from the controller to the individual devices in the system via one or more networks.

At block 1112, the user may enter a scene selection menu and select the "bedroom" scene to activate from a list or set of stored scenes. Prior to activating the "bedroom" scene, the scent diffusing device may confirm that oils required for the scent are available in sufficient quantities for the recipe. If insufficient quantities are available, the scent diffusing device may send an indication of an error to the user that updates available oil components in the system. The user may select from the updated list of available scents. At block 1114, the scent diffusing device(s) may release the scent at the specified release time according to the scent scene settings and may be done concurrently with playback of the media content saved in the scene.

Figure 12:
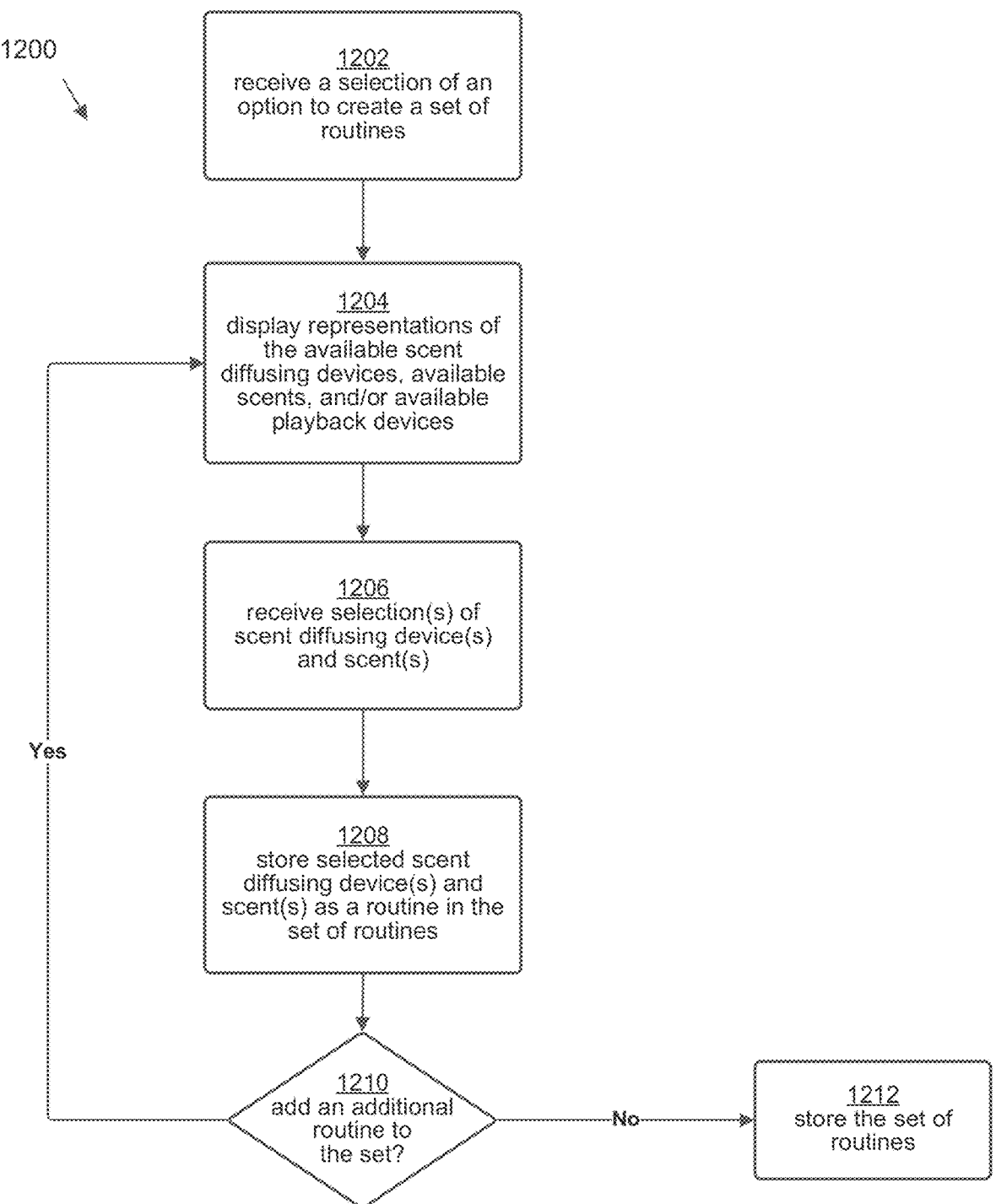
FIG. 12 shows an example method of creating a set of routines.

FIG. 12 shows an illustrative method 1200 for creating a set of routines. At block 1202, the user may select an option to create a set of routines. At block 1204, the system can identify available scent diffusing devices in the system for scent diffusion and/or playback devices for media content playback and available scents for diffusion as described herein. The available scents and devices can be displayed to user for use in a first routine of the set of routines. At 1206, the system can receive from the user selection(s) of the scent diffusion device(s) and scent(s) to diffuse for the first routine. In the event the user desires for there to be media playback with the first routine, the user may select scent diffusion devices that are capable of media playback and/or playback devices. At block 1208, the system can store the selected scent diffusing device(s), playback device(s), and/or scents as the first routine in the set of routine.

At block 1210, the user can indicate whether to add another routine within the set of routines. If yes, then the method 1200 proceeds back to block 1204 to receive selections and settings for the second routine in the set. If the user is finished with the routine, the method 1200 may proceed to block 1212 where the routine is saved. A name for the routine may be stored with the routine for later selection by the user.

CONCLUSION

The description above discloses, among other things, various example systems, methods, apparatus, and articles of manufacture including, among other components, firmware and/or software executed on hardware. It is understood that such examples are merely illustrative and should not be considered as limiting. For example, it is contemplated that any or all of the firmware, hardware, and/or software aspects or components can be embodied exclusively in hardware, exclusively in software, exclusively in firmware, or in any combination of hardware, software, and/or firmware. Accordingly, the examples provided are not the only way(s) to implement such systems, methods, apparatus, and/or articles of manufacture.

The specification is presented largely in terms of illustrative environments, systems, procedures, steps, logic blocks, processing, and other symbolic representations that directly or indirectly resemble the operations of data processing devices coupled to networks. These process descriptions and representations are typically used by those skilled in the art to most effectively convey the substance of their work to others skilled in the art. Numerous specific details are set forth to provide a thorough understanding of the present disclosure. However, it is understood to hose skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the forgoing description of embodiments.

When any of the appended claims are read to cover a purely software and/or firmware implementation, at least one of the elements in at least one example is hereby expressly defined to include a tangible, non-transitory medium such as a memory, DVD, CD, Blu-ray, and so on, storing the software and/or firmware.

The invention claimed is:
1. A controller device, comprising:
at least one processor; and a tangible, non-transitory computer-readable medium comprising program instructions that are executable by the at least one processor such that the controller device is configured to:

receive an input to initiate creation of a scent scene for activation by a combined scent-diffusing and media-playback system;

display one or more representations of scent diffusing devices;

receive input, via selection of a first representation of the one or more representations of scent diffusing devices, that indicates a selection of a first scent diffusing device for the scent scene;

receive input selecting a particular scent for the first scent diffusing device to release for the scent scene;

display one or more representations of playback devices;

receive input, via selection of a first representation of the one or more representations of playback devices, that indicates a selection of a first playback device for the scent scene;

receive input selecting particular media content for the first playback device to play back for the scent scene;

cause information defining the scent scene to be stored in a computing system remote to the controller device;

receive input selecting the scent scene for activation; and in response to receiving the input selecting the scent scene for activation:

based on the information defining the scent scene, send, to the first scent diffusing device, a message comprising information indicating the particular scent to release;

cause the first scent diffusing device to release the particular scent;

based on the information defining the scent scene, send, to the first playback device, a message comprising information indicating the particular media content; and cause the first playback device to play back the particular media content.

2. The controller device of claim 1, wherein the program instructions are executable by the at least one processor such that the controller device is further configured to:

receive, via the first scent diffusing device, canister information indicating one or more canisters containing scented oil for diffusion, the canister information comprising a name for each canister;

receive a selection of a scent recipe creation option;

display the name for each of the one or more canisters;

receive one or more inputs selecting a first canister and a second canister of the one or more canisters to include in a recipe for the particular scent; and cause the recipe to be stored in a computing system remote to the controller device.

3. The controller device of claim 1, wherein the program instructions that are executable by the at least one processor such that the controller device is configured to display one or more representations of scent diffusing devices comprise program instructions that are executable by the at least one processor such that the controller device is configured to:

display representations of the first scent diffusing device and a second scent diffusing device; and wherein the program instructions are executable by the at least one processor such that the controller device is further configured to:

receive input selecting the second scent diffusing device for the scent scene;

obtain information indicating scents available for diffusion;

display a name of the particular scent and a name of a second scent;

receive input indicating a name for the scent scene; and associate the first scent diffusing device, the second scent diffusing device, and the particular scent.

4. The controller device of claim 3, wherein the program instructions are executable by the at least one processor such that the controller device is further configured to:

in response to receiving the input selecting the scent scene:

based on the information defining the scent scene, send, to the second scent diffusing device, the message comprising information indicating the particular scent to release; and wherein the program instructions that are executable by the at least one processor such that the controller device is configured to cause the first scent diffusing device to release the particular scent comprise program instructions that are executable by the at least one processor such that the controller device is configured to:

cause the first scent diffusing device and the second scent diffusing device to concurrently release the particular scent.

5. The controller device of claim 1, wherein the program instructions are executable by the at least one processor such that the controller device is further configured to:

receive a selection of an option to create a set of routines, the set comprising a first routine and a second routine;

display representations of the first scent diffusing device and a second scent diffusing device;

receive one or more first inputs indicating the first scent diffusing device and the second scent diffusing device as one or more diffusing devices for the first routine;

obtain information identifying scents available for diffusion;

based on the obtained information, display a name of the particular scent and a name of the second scent;

receive a selection of the particular scent as a scent for the first routine;

associate the first scent diffusing device, the second scent diffusing device, and the particular scent with the first routine;

receive an input specifying an execution time for the first routine; and store the first routine in association with the set of routines.

6. The controller device of claim 5, wherein the program instructions are executable by the at least one processor such that the controller device is further configured to:

receive one or more second inputs indicating the first scent diffusing device and the second scent diffusing device as one or more diffusing devices for the second routine;

based on the obtained information, display a name of the particular scent and a name of the second scent;

receive a selection of the second scent as a scent for the second routine;

associate the first scent diffusing device, the second scent diffusing device, and the second scent with the second routine;

receive an input specifying an execution time for the second routine; and store the second routine in association with the set of routines.

7. A tangible, non-transitory computer-readable medium comprising program instructions that are executable by at least one processor such that a controller device is configured to:

receive an input to initiate creation of a scent scene for activation by a combined scent-diffusing and media-playback system;

display-one or more representations of scent diffusing devices;

receive input, via selection of a first representation of the one or more representations of scent diffusing devices, that indicates a selection of a first scent diffusing device for the scent scene;

receive input selecting a particular scent for the first scent diffusing device to release for the scent scene;

display one or more representations of playback devices;

receive input, via selection of a first representation of the one or more representations of playback devices, that indicates a selection of a first playback device for the scent scene;

receive input selecting particular media content for the first playback device to play back for the scent scene;

cause information defining the scent scene to be stored in a computing system remote to the controller device;

receive input selecting the scent scene for activation; and in response to receiving the input selecting the scent scene for activation:

based on the information defining the scent scene, send, to the first scent diffusing device, a message comprising information indicating the particular scent to release;

cause the first scent diffusing device to release the particular scent;

based on the information defining the scent scene, send, to the first playback device, a message comprising information indicating the particular media content; and cause the first playback device to play back the particular media content.

8. The tangible, non-transitory computer-readable medium of claim 7, wherein the program instructions are executable by the at least one processor such that the controller device is further configured to:

receive, via the first scent diffusing device, canister information indicating one or more canisters containing scented oil for diffusion, the canister information comprising a name for each canister;

receive a selection of a scent recipe creation option;

display the name for each of the one or more canisters;

receive one or more inputs selecting a first canister and a second canister of the one or more canisters to include in a recipe for the particular scent; and cause the recipe to be stored in a computing system remote to the controller device.

9. The tangible, non-transitory computer-readable medium of claim 7, wherein the program instructions that are executable by the at least one processor such that the controller device is configured to display one or more representations of scent diffusing devices comprise program instructions that are executable by the at least one processor such that the controller device is configured to:

display representations of the first scent diffusing device and a second scent diffusing device; and wherein the program instructions are executable by the at least one processor such that the controller device is further configured to:

receive input selecting the second scent diffusing device for the scent scene;

obtain information indicating scents available for diffusion;

display a name of the particular scent and a name of a second scent;

receive input indicating a name for the scent scene; and associate the first scent diffusing device, the second scent diffusing device, and the particular scent.

10. The tangible, non-transitory computer-readable medium of claim 9, wherein the program instructions are executable by the at least one processor such that the controller device is further configured to:

in response to receiving the input selecting the scent scene:

based on the information defining the scent scene, send, to the second scent diffusing device, the message comprising information indicating the particular scent to release; and wherein the program instructions that are executable by the at least one processor such that the controller device is configured to cause the first scent diffusing device to release the particular scent comprise program instructions that are executable by the at least one processor such that the controller device is configured to:

cause the first scent diffusing device and the second scent diffusing device to concurrently release the particular scent.

11. The tangible, non-transitory computer-readable medium of claim 7, wherein the program instructions are executable by the at least one processor such that the controller device is further configured to:

receive a selection of an option to create a set of routines, the set comprising a first routine and a second routine;

display representations of the first scent diffusing device and a second scent diffusing device;

receive one or more first inputs indicating the first scent diffusing device and the second scent diffusing device as one or more diffusing devices for the first routine;

obtain information identifying scents available for diffusion;

based on the obtained information, display a name of the particular scent and a name of the second scent;

receive a selection of the particular scent as a scent for the first routine;

associate the first scent diffusing device, the second scent diffusing device, and the particular scent with the first routine;

receive an input specifying an execution time for the first routine; and store the first routine in association with the set of routines.

12. The tangible, non-transitory computer-readable medium of claim 11, wherein the program instructions are executable by the at least one processor such that the controller device is further configured to:

receive one or more second inputs indicating the first scent diffusing device and the second scent diffusing device as one or more diffusing devices for the second routine;

based on the obtained information, display a name of the particular scent and a name of the second scent;

receive a selection of the second scent as a scent for the second routine;

associate the first scent diffusing device, the second scent diffusing device, and the second scent with the second routine;

receive an input specifying an execution time for the second routine; and store the second routine in association with the set of routines.

13. A method carried out by a controller device, the method comprising:

receiving an input to initiate creation of a scent scene for activation by a combined scent-diffusing and media-playback system;

displaying one or more representations of scent diffusing devices;

receiving input, via selection of a first representation of the one or more representations of scent diffusing devices, that indicates a selection of a first scent diffusing device for the scent scene;

receiving input selecting a particular scent for the first scent diffusing device to release for the scent scene;

displaying one or more representations of playback devices;

receiving input, via selection of a first representation of the one or more representations of playback devices, that indicates a selection of a first playback device for the scent scene;

receiving input selecting particular media content for the first playback device to play back for the scent scene;

causing information defining the scent scene to be stored in a computing system remote to the controller device;

receiving input selecting the scent scene for activation; and in response to receiving the input selecting the scent scene for activation:

based on the information defining the scent scene, sending, to the first scent diffusing device, a message comprising information indicating the particular scent to release;

causing the first scent diffusing device to release the particular scent;

based on the information defining the scent scene, sending, to the first playback device, a message comprising information indicating the particular media content; and causing the first playback device to play back the particular media content.

14. The method of claim 13, further comprising:

receiving, via the first scent diffusing device, canister information indicating one or more canisters containing scented oil for diffusion, the canister information comprising a name for each canister;

receiving a selection of a scent recipe creation option;

displaying the name for each of the one or more canisters;

receiving one or more inputs selecting a first canister and a second canister of the one or more canisters to include in a recipe for the particular scent; and causing the recipe to be stored in a computing system remote to the controller device.

15. The method of claim 13, wherein displaying one or more representations of scent diffusing devices comprises displaying representations of the first scent diffusing device and a second scent diffusing device, the method further comprising:

receiving input selecting the second scent diffusing device for the scent scene;

obtaining information indicating scents available for diffusion;

displaying a name of the particular scent and a name of a second scent;

receiving input indicating a name for the scent scene; and associating the first scent diffusing device, the second scent diffusing device, and the particular scent.

16. The controller device of claim 1, wherein the program instructions are executable by the at least one processor such that the controller device is further configured to:

display at least one setting for the particular scent; and receive input selecting a first setting of the at least one setting for the scent scene, wherein the program instructions that are executable by the at least one processor such that the controller device is configured to cause the information defining the scent scene to be stored in the computing system remote to the controller device comprise program instructions that are executable by the at least one processor such that the controller device is configured to:

cause the information defining the scent scene to be stored in the computing system remote to the controller device, the information comprising the first setting, wherein the program instructions that are executable by the at least one processor such that the controller device is configured to send, to the first scent diffusing device, a message comprising information indicating the particular scent to release comprise program instructions that are executable by the at least one processor such that the controller device is configured to:

based on the information defining the scent scene, send, to the first scent diffusing device, a message comprising information indicating the particular scent to release and the first setting, and wherein the program instructions that are executable by the at least one processor such that the controller device is configured to cause the first scent diffusing device to release the particular scent comprise program instructions that are executable by the at least one processor such that the controller device is configured to:

cause the first scent diffusing device to release the particular scent in accordance with the first setting.

17. The controller device of claim 16, wherein the at least one setting comprises at least one of a scent release time, a duration of scent release, or a scent strength setting.

18. The controller device of claim 1, wherein the program instructions are executable by the at least one processor such that the controller device is further configured to:

in response to receiving the input selecting the scent scene for activation:

retrieve the information defining the scent scene from the computing system remote to the controller device.

19. The tangible, non-transitory computer-readable medium of claim 7, wherein the program instructions are executable by the at least one processor such that the controller device is further configured to:

display at least one setting for the particular scent; and receive input selecting a first setting of the at least one setting for the scent scene, wherein the program instructions that are executable by the at least one processor such that the controller device is configured to cause the information defining the scent scene to be stored in the computing system remote to the controller device comprise program instructions that are executable by the at least one processor such that the controller device is configured to:

cause the information defining the scent scene to be stored in the computing system remote to the controller device, the information comprising the first setting, wherein the program instructions that are executable by the at least one processor such that the controller device is configured to send, to the first scent diffusing device, a message comprising information indicating the particular scent to release comprise program instructions that are executable by the at least one processor such that the controller device is configured to:

based on the information defining the scent scene, send, to the first scent diffusing device, a message comprising information indicating the particular scent to release and the first setting, and wherein the program instructions that are executable by the at least one processor such that the controller device is configured to cause the first scent diffusing device to release the particular scent comprise program instructions that are executable by the at least one processor such that the controller device is configured to:

cause the first scent diffusing device to release the particular scent in accordance with the first setting.

20. The tangible, non-transitory computer-readable medium of claim 18, wherein the at least one setting comprises at least one of a scent release time, a duration of scent release, or a scent strength setting.

* * * * *